United States Patent
Eylem et al.

(10) Patent No.: US 9,492,808 B2
(45) Date of Patent: Nov. 15, 2016

(54) ABSORBENT FIBROUS STRUCTURES COMPRISING A POLYMERIC FLUID COMPRISING A SOIL ADSORBING AGENT

(71) Applicant: The Procter & Gamble Company, Cincinnati, OH (US)

(72) Inventors: Cahit Eylem, West Chester, OH (US); Michael Scott Prodoehl, West Chester, OH (US); Charles William Neal, Fairfield, OH (US); Jeffrey Glen Sheehan, Symmes Township, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 14/862,185

(22) Filed: Sep. 23, 2015

(65) Prior Publication Data

US 2016/0082412 A1    Mar. 24, 2016

Related U.S. Application Data

(60) Provisional application No. 62/054,082, filed on Sep. 23, 2014.

(51) Int. Cl.
| | | |
|---|---|---|
| *B01J 20/22* | (2006.01) | |
| *B01J 20/26* | (2006.01) | |
| *B01J 20/24* | (2006.01) | |
| *B01J 20/28* | (2006.01) | |
| *B01J 20/32* | (2006.01) | |
| *A47L 13/17* | (2006.01) | |
| *A61K 8/02* | (2006.01) | |
| *C11D 3/37* | (2006.01) | |
| *C11D 17/04* | (2006.01) | |
| *D21H 21/22* | (2006.01) | |

(52) U.S. Cl.
CPC .............. *B01J 20/261* (2013.01); *A47L 13/17* (2013.01); *A61K 8/0208* (2013.01); *B01J 20/24* (2013.01); *B01J 20/28023* (2013.01); *B01J 20/28033* (2013.01); *B01J 20/3287* (2013.01); *C11D 3/37* (2013.01); *C11D 3/3769* (2013.01); *C11D 17/049* (2013.01); *D21H 21/22* (2013.01)

(58) Field of Classification Search
CPC ........................................................ B01J 20/22
USPC ........................................................ 502/401
See application file for complete search history.

(56) References Cited

U.S. PATENT DOCUMENTS

| | | |
|---|---|---|
| 2010/0212849 A1 | 8/2010 | Smith et al. |
| 2012/0055643 A1 | 3/2012 | Neal et al. |
| 2013/0255015 A1 | 10/2013 | Neal et al. |

FOREIGN PATENT DOCUMENTS

WO    WO-2008/156454 A1    12/2008

OTHER PUBLICATIONS

PCT International Search Report dated Nov. 26, 2015—6 pages.
PCT International Search Report dated Nov. 17, 2015—6 pages.

*Primary Examiner* — Edward Johnson
(74) *Attorney, Agent, or Firm* — C. Brant Cook

(57) ABSTRACT

Absorbent fibrous structure containing a polymeric fluid containing a polymer, including for example a copolymer and/or terpolymer, soil adsorbing agent, and absorbent fibrous structures containing such polymer soil adsorbing agents, and methods for making same.

20 Claims, No Drawings

ABSORBENT FIBROUS STRUCTURES COMPRISING A POLYMERIC FLUID COMPRISING A SOIL ADSORBING AGENT

FIELD OF THE INVENTION

The present invention relates to absorbent fibrous structure comprising a polymeric fluid comprising a polymer, including for example a copolymer and/or terpolymer, soil adsorbing agent, and absorbent fibrous structures comprising such polymer soil adsorbing agents, and methods for making same.

BACKGROUND OF THE INVENTION

Fibrous structures comprising a polymer soil adsorbing agent are known. For example, water-based polymeric fluids comprising a polymer soil adsorbing agent have been delivered to fibrous structures in the past. Further, oil-based polymeric fluids, for example emulsions, such as inverse emulsions and/or dewatered inverse emulsions, comprising a soil adsorbing agent, have been delivered to fibrous structures in the past. However, such polymer soil adsorbing agents in the past have been generally linear polymers, for example linear polyacrylamides, and have typically exhibited higher weight average molecular weights, for example greater than 4,000,000 and/or to about 40,000,000 g/mol and lower charge densities, for example between −0.1 and +0.1 meq/g. It has been found that such known polymer soil adsorbing agents, in particular, linear polymers, for example linear polyacrylamide, can exhibit an adhesive sensorial feel to consumers during use. In addition such known polymer soil adsorbing agents tend to exhibit chemical instability and polymer rigidity. In addition to the material issues, the current processes for producing the known fibrous structures utilize high levels of soil adsorbing agents, for example 50% or more by weight. These high levels of soil adsorbing agents create processing nightmares when applying the soil adsorbing agent to a fibrous structure. One major issue with the use of high levels of soil adsorbing agents is hard buildup on rollers, which creates web handling issues such as loss of web control and/or loss of traction of the web during the application of the soil adsorbing agent from the applicator through log winding in a fibrous structure converting line. Another issue with the use of high levels of soil adsorbing agents is clogging of delivery equipment, such as slot extruders, and/or non-uniform delivery of the soil adsorbing agents during application to the fibrous structures. Yet another issue with the use of high levels of soil adsorbing agents is clogging perforation blades. In general, the high levels of soil adsorbing agents creates a sticky mess throughout the application and winding process.

In addition to the processing problems, the presence of high levels of soil adsorbing agents on a fibrous structure suppresses absorbency properties of the fibrous structure, for example significantly decreases the CRT Initial Rate for the fibrous structure compared to the CRT Initial Rate of the fibrous structure without the soil adsorbing agents.

One problem with current fibrous structures comprising a known polymer soil adsorbing agent is that the soil adsorbing agent exhibits an adhesive, for example a sticky and/or tacky, sensorial feel to consumers during use of the fibrous structures. In addition, current processes for making such fibrous structures comprising a known polymer soil adsorbing agent using high levels (50% or greater by weight) creates significant hygiene issues and absorbency negatives as described above.

Accordingly, there is a need for a fibrous structure comprising a polymer soil adsorbing agent that doesn't exhibit the negatives described above; namely, doesn't exhibit an adhesive sensorial feel to consumers during use, doesn't exhibit chemical instability, doesn't exhibit polymer rigidity, and/or doesn't create hygiene issues delivery of such polymer soil adsorbing agent to fibrous structure during the making of such fibrous structures.

SUMMARY OF THE INVENTION

The present invention fulfills the needs described above by providing a fibrous structure comprising a polymer soil adsorbing agent that overcomes the negatives described above and is made by a process that overcomes the hygiene issues described above.

One solution to the problem identified above is a fibrous structure comprising a polymer, for example a copolymer, such as a branched copolymer soil adsorbing agent, at a lower level (less than 37% and/or less than 30% and/or greater than 10% and/or greater than 15% and/or greater than 20% by weight) of a soil adsorbing agent and a process for making a fibrous structure that utilizes a polymeric fluid comprising a lower level (less than 37% and/or less than 30% and/or greater than 10% and/or greater than 15% and/or greater than 20% by weight) of a soil adsorbing agent such that the adhesive sensorial feel negatives, absorbency negatives and hygiene issues described above are overcome. The polymer soil adsorbing agent exhibits a lower weight average molecular weight (less than 6,000,000 g/mol and/or less than 2,000,000 g/mol and/or less than 1,000,000 g/mol and/or less than 800,000 g/mol) and/or exhibits a high charge (greater than 0 and/or greater than 2 and/or greater than 4 and/or greater than 6 and/or greater than 8 meq/g).

In one example of the present invention, an absorbent fibrous structure comprising a polymeric fluid comprising a polymer comprising two or more different monomeric units, for example a copolymer, such as a branched copolymer, soil adsorbing agent that exhibits a weight average molecular weight (and/or absolute molecular weight of an aqueous polymer) of greater than 50,000 g/mol to less than 6,000,000 g/mol as measured according to the Molecular Weight Test Method described herein and a charge density of greater than 0 meq/g as measured according to the Charge Density Test Method described herein is provided.

In still another example of the present invention, a single- or multi-ply sanitary tissue product comprising an absorbent fibrous structure according to the present invention.

In yet another example of the present invention, a method for making an absorbent fibrous structure comprising the step of contacting an absorbent fibrous structure with a polymeric fluid comprising a polymer, for example a copolymer, such as a branched copolymer soil adsorbing agent that exhibits a weight average molecular weight (and/or absolute molecular weight of an aqueous polymer) of greater than 50,000 g/mol to less than 6,000,000 g/mol as measured according to the Molecular Weight Test Method described herein and a charge density of greater than 0 meq/g as measured according to the Charge Density Test Method described herein is provided. In one example, the polymer soil adsorbing agent is delivered to the fibrous structure in the form of a polymeric fluid selected from the group consisting of: an aqueous solution, a dispersion or emulsion, for example an inverse dispersion or emulsion and/or a dewatered inverse dispersion or emulsion, a powder, a hydrogel, an inverted hydrogel, and mixtures thereof.

The present invention provides novel absorbent fibrous structures comprising a polymer, for example a copolymer, such as a branched copolymer soil adsorbing agent and methods for making same.

DETAILED DESCRIPTION OF THE INVENTION

Definitions

"Fibrous structure" as used herein means a structure that comprises one or more fibrous filaments and/or fibers. In one example, a fibrous structure according to the present invention means an orderly arrangement of filaments and/or fibers within a structure in order to perform a function. Non-limiting examples of fibrous structures of the present invention include paper, fabrics (including woven, knitted, and non-woven), and absorbent pads (for example for diapers or feminine hygiene products).

Non-limiting examples of processes for making fibrous structures include known wet-laid processes, such as wet-laid papermaking processes, and air-laid processes, such as air-laid papermaking processes. Wet-laid and/or air-laid papermaking processes typically include a step of preparing a composition comprising a plurality of fibers that are suspended in a medium, either wet, more specifically aqueous medium, or dry, more specifically gaseous medium, such as air. The aqueous medium used for wet-laid processes is oftentimes referred to as a fiber slurry. The fiber composition is then used to deposit a plurality of fibers onto a forming wire or belt such that an embryonic fibrous structure is formed, after which drying and/or bonding the fibers together results in a fibrous structure. Further processing the fibrous structure may be carried out such that a finished fibrous structure is formed. For example, in typical papermaking processes, the finished fibrous structure is the fibrous structure that is wound on the reel at the end of papermaking, and may subsequently be converted into a finished product, e.g. a sanitary tissue product.

Non-limiting examples of other known processes and/or unit operations for making fibrous structures include fabric crepe and/or belt crepe processes, ATMOS processes, NTT processes, through-air-dried processes, uncreped through-air-dried processes, and conventional wet press processes.

Another process that can be used to produce the fibrous structures is a melt-blowing, dry spinning, and/or spunbonding process where a polymer composition is spun into filaments and collected on a belt to produce a fibrous structure. In one example, a plurality of fibers may be mixed with the filaments prior to collecting on the belt and/or a plurality of fibers may be deposited on a prior produced fibrous structure comprising filaments.

The fibrous structures of the present invention may be homogeneous or may be layered in the direction normal to the machine direction. If layered, the fibrous structures may comprise at least two and/or at least three and/or at least four and/or at least five layers.

The fibrous structures of the present invention may be co-formed fibrous structures. "Co-formed" as used herein means that the fibrous structure comprises a mixture of at least two different components wherein at least one of the components comprises a filament, such as a polypropylene filament, and at least one other component, different from the first component, comprises a solid additive, such as a fiber and/or a particulate. In one example, a co-formed fibrous structure comprises solid additives, such as fibers, such as wood pulp fibers and/or absorbent gel articles of manufacture and/or filler particles and/or particulate spot bonding powders and/or clays, and filaments, such as polypropylene filaments.

"Solid additive" as used herein means a fiber and/or a particulate.

"Particulate" as used herein means a granular substance or powder.

"Fiber" and/or "Filament" as used herein means an elongate particulate having an apparent length greatly exceeding its apparent width, i.e. a length to diameter ratio of at least about 10. In one example, a "fiber" is an elongate particulate as described above that exhibits a length of less than 5.08 cm (2 in.) and a "filament" is an elongate particulate as described above that exhibits a length of greater than or equal to 5.08 cm (2 in.).

Fibers are typically considered discontinuous in nature. Non-limiting examples of fibers include wood pulp fibers and synthetic staple fibers such as polyester fibers.

Filaments are typically considered continuous or substantially continuous in nature. Filaments are relatively longer than fibers. Non-limiting examples of filaments include meltblown and/or spunbond filaments. Non-limiting examples of articles of manufacture that can be spun into filaments include natural polymers, such as starch, starch derivatives, cellulose and cellulose derivatives, hemicellulose, hemicellulose derivatives, and synthetic polymers including, but not limited to polyvinyl alcohol filaments and/or polyvinyl alcohol derivative filaments, and thermoplastic polymer filaments, such as polyesters, nylons, polyolefins such as polypropylene filaments, polyethylene filaments, and biodegradable or compostable thermoplastic fibers such as polylactic acid filaments, polyhydroxyalkanoate filaments and polycaprolactone filaments. The filaments may be monocomponent or multicomponent, such as bicomponent filaments.

In one example of the present invention, "fiber" refers to papermaking fibers. Papermaking fibers useful in the present invention include cellulosic fibers commonly known as wood pulp fibers. Applicable wood pulps include chemical pulps, such as Kraft, sulfite, and sulfate pulps, as well as mechanical pulps including, for example, groundwood, thermomechanical pulp and chemically modified thermomechanical pulp. Chemical pulps, however, may be preferred since they impart a superior tactile sense of softness to tissue sheets made therefrom. Pulps derived from both deciduous trees (hereinafter, also referred to as "hardwood") and coniferous trees (hereinafter, also referred to as "softwood") may be utilized. The hardwood and softwood fibers can be blended, or alternatively, can be deposited in layers to provide a stratified web. Also applicable to the present invention are fibers derived from recycled paper, which may contain any or all of the above categories as well as other non-fibrous articles of manufacture such as fillers and adhesives used to facilitate the original papermaking.

In addition to the various wood pulp fibers, other cellulosic fibers such as cotton linters, rayon, lyocell and bagasse can be used in this invention. Other sources of cellulose in the form of fibers or capable of being spun into fibers include grasses and grain sources.

"Absorbent fibrous structure" as used herein means a fibrous structure that absorbs water.

"Dry web" as used herein means a web that comprises less than 30% and/or less than 20% and/or less than 15% and/or less than 10% and/or less than 7% and/or less than 5% and/or less than 3% and/or less than 2% and less than 1% and/or less than 0.5% by weight of moisture as measured according to the Moisture Content Test Method described herein.

"Dry absorbent fibrous structure" as used herein means an absorbent fibrous structure that comprises less than 30% and/or less than 20% and/or less than 15% and/or less than 10% and/or less than 7% and/or less than 5% and/or less than 3% and/or less than 2% and/or less than 1% and/or less than 0.5% by weight of moisture as measured according to the Moisture Content Test Method described herein.

"Sanitary tissue product" as used herein means a soft, low density (i.e. <about 0.15 g/cm$^3$) web useful as a wiping implement for post-urinary and post-bowel movement cleaning (toilet tissue), for otorhinolaryngological discharges (facial tissue), multi-functional absorbent and cleaning uses (absorbent towels), and folded sanitary tissue products such as napkins and/or facial tissues including folded sanitary tissue products dispensed from a container, such as a box. The sanitary tissue product may be convolutedly wound upon itself about a core or without a core to form a sanitary tissue product roll.

In one example, the sanitary tissue product of the present invention comprises a fibrous structure according to the present invention.

The sanitary tissue products of the present invention may exhibit a basis weight between about 10 g/m$^2$ to about 120 g/m$^2$ and/or from about 15 g/m$^2$ to about 110 g/m$^2$ and/or from about 20 g/m$^2$ to about 100 g/m$^2$ and/or from about 30 to 90 g/m$^2$ as measured according to the Basis Weight Test Method described herein. In addition, the sanitary tissue product of the present invention may exhibit a basis weight between about 40 g/m$^2$ to about 120 g/m$^2$ and/or from about 50 g/m$^2$ to about 110 g/m$^2$ and/or from about 55 g/m$^2$ to about 105 g/m$^2$ and/or from about 60 to 100 g/m$^2$ as measured according to the Basis Weight Test Method described herein.

The sanitary tissue products of the present invention may be in the form of sanitary tissue product rolls. Such sanitary tissue product rolls may comprise a plurality of connected, but perforated sheets of fibrous structure, that are separably dispensable from adjacent sheets. In one example, one or more ends of the roll of sanitary tissue product may comprise an adhesive and/or dry strength agent to mitigate the loss of fibers, especially wood pulp fibers from the ends of the roll of sanitary tissue product.

The sanitary tissue products of the present invention may comprise additives such as softening agents, temporary wet strength agents, permanent wet strength agents, bulk softening agents, lotions, silicones, wetting agents, latexes, especially surface-pattern-applied latexes, dry strength agents such as carboxymethylcellulose and starch, and absorbency aids.

"Basis Weight" as used herein is the weight per unit area of a sample reported in lbs/3000 ft$^2$ or g/m$^2$ and is measured according to the Basis Weight Test Method described herein.

"By weight of moisture" or "moisture content" means the amount of moisture present in an article of manufacture measured according to the Moisture Content Test Method described herein immediately after the article of manufacture has been conditioned in a conditioned room at a temperature of 73° F.±4° F. (about 23° C.±2.2° C.) and a relative humidity of 50%±10% for at least 2 hours.

"Water-soluble" as used herein means a material, such as a polymer, for example a soil adsorbing polymer that is miscible in water. In other words, a material that is capable of forming a stable (does not separate for greater than 5 minutes after forming the homogeneous solution) homogeneous solution with water at ambient conditions (about 23° C. and a relative humidity of about 50%).

"Machine Direction" or "MD" as used herein means the direction parallel to the flow of the fibrous structure making machine and/or sanitary tissue product manufacturing equipment.

"Cross Machine Direction" or "CD" as used herein means the direction parallel to the width of the fibrous structure making machine and/or sanitary tissue product manufacturing equipment and perpendicular to the machine direction.

"Ply" as used herein means an individual, integral fibrous structure.

"Plies" as used herein means two or more individual, integral fibrous structures disposed in a substantially contiguous, face-to-face relationship with one another, forming a multi-ply fibrous structure and/or multi-ply sanitary tissue product. It is also contemplated that an individual, integral fibrous structure can effectively form a multi-ply fibrous structure, for example, by being folded on itself.

Absorbent Fibrous Structure

In one example of the present invention, the absorbent fibrous structure comprises a polymer, for example a copolymer, such as a branched copolymer soil adsorbing agent, for example in the form of a plurality of water-soluble soil adsorbing polymer particles, wherein the polymer soil adsorbing agent exhibits a weight average molecular weight (and/or absolute molecular weight of an aqueous polymer) of greater than 50,000 g/mol to less than 6,000,000 g/mol and/or greater than 100,000 g/mol to less than 2,000,000 g/mol and/or greater than 100,000 g/mol to less than 1,000,000 g/mol and/or greater than 100,000 g/mol to less than 1,000,000 g/mol and/or greater than 300,000 g/mol to less than 1,000,000 g/mol and/or greater than 500,000 g/mol to less than 1,000,000 g/mol and/or greater than 500,000 g/mol to less than 800,000 g/mol and/or less than 750,00 g/mol as measured according to the Molecular Weight Test Method described herein and a charge density of greater than 0 meq/g and/or greater than 2 meq/g and/or greater than 4 meq/g and/or greater than 6 meq/g and/or greater than 8 meq/ as measured according to the Charge Density Test Method described herein.

In one example, the absorbent fibrous structure comprises a dewatered emulsion comprising a polymer, for example a copolymer, such as a branched copolymer soil adsorbing agent, for example in the form of a plurality of water-soluble soil adsorbing polymer particles, and a hydrocarbon fluid, for example a hydrocarbon fluid that exhibits a VOC content of less than 60% as measured according to the VOC Test Method described herein.

In one example, the absorbent fibrous structure of the present invention comprises a dry absorbent fibrous structure such as a dry paper towel, rather than a pre-moistened, liquid composition-containing towel or wipe or pad.

In one example, the absorbent fibrous structure of the present invention exhibits an Average Soil Adsorption Value of greater than 90 and/or greater than 100 and/or greater than 110 and/or greater than 125 and/or greater than 150 and/or greater than 175 and/or greater than 200 mg Soil/g of Absorbent Fibrous Structure as measured according to the Soil Adsorption Test Method described herein before (initially) and after being subjected to the Accelerated and Stress Aging Procedures described herein.

In another example, the absorbent fibrous structure of the present invention exhibits an Average Mirror Cleaning Densitometer Value of greater than −0.5 and/or greater than −0.45 and/or greater than −0.38 and/or greater than −0.30 and/or greater than −0.25 and/or greater than −0.20 and/or greater than −0.15 as measured according to the Mirror Cleaning Test Method described herein before (initially) and after being subjected to the Accelerated and Stress Aging Procedures described herein.

It has been unexpectedly found that absorbent fibrous structures comprising a dispersion or emulsion comprising a polymer, for example a copolymer, such as a branched copolymer soil adsorbing agent according to the present invention exhibit a CRT Initial Rate of greater than 0.15 g/second and/or greater than 0.20 g/second and/or greater than 0.30 g/second and/or greater than 0.40 g/second as measured according to the CRT Test Method described herein. It has further unexpectedly been found that absorbent fibrous structures comprising a polymer, for example a copolymer, such as a branched copolymer soil adsorbing agent according to the present invention exhibit a CRT Initial Rate Change of less than 50% and/or less than 40% and/or less than 30% and/or less than 20% and/or less than 15% and/or less than 10% and/or less than 5% as measured according to the CRT Test Method described herein.

The absorbent fibrous structure may be a dry absorbent fibrous structure.

The absorbent fibrous structure of the present invention may comprise a plurality of pulp fibers. Further, the absorbent fibrous structure of the present invention may comprise a single-ply or multi-ply sanitary tissue product, such as a paper towel.

In another example, the absorbent fibrous structure may be in the form of a cleaning pad suitable for use with a cleaning device, such as a floor cleaning device, for example a Swiffer® cleaning pad or equivalent cleaning pads.

In still another example, the polymer, for example a copolymer, such as a branched copolymer soil adsorbing agent may be present in a liquid, such as a cleaning composition comprising water and/or a surfactant and/or a hydrocarbon fluid, which may be used with a fibrous structure comprising or void of a dispersion or emulsion according to the present invention.

In one example, the polymer, for example a copolymer, such as a branched copolymer soil adsorbing agent for example in the form of polymer particles, present in the dispersion or emulsion on and/or in the absorbent fibrous structure of the present invention may be present in and/or on an absorbent fibrous structure in a pattern, such as a non-random repeating pattern composing lines and or letters/words, and/or present in and/or on regions of different density, different basis weight, different elevation and/or different texture of the absorbent fibrous structure. In one example, the polymer, for example copolymer, such as a branched copolymer soil adsorbing agent, for example in the form of soil adsorbing polymer particles, present in and/or on an absorbent fibrous structure of the present invention may provide a visual signal resulting from an increased concentration of soil adsorbed onto the polymer soil adsorbing agent, for example onto the soil adsorbing polymer particle.

In addition to the polymer, for example a copolymer, such as a branched copolymer soil adsorbing agent, for example in the form of soil adsorbing polymer particles, the dispersion or emulsion on and/or in the absorbent fibrous structure may comprise other ingredients, for example one or more surfactants. The surfactants may be present in and/or on the absorbent fibrous structure at a level of from about 0.01% to about 0.5% by weight of the absorbent fibrous structure. Non-limiting examples of suitable surfactants include $C_{8-16}$ alkyl polyglucoside, cocoamido propyl sulfobetaine, and mixtures thereof.

In one example, the absorbent fibrous structure comprises a signal, such as a dye and/or pigment, that becomes visible or becomes invisible to a consumer's eye when the absorbent fibrous structure adsorbs soil and/or when a soil adsorbing agent, for example a soil adsorbing polymer particle, present in and/or on the absorbent fibrous structure adsorbs soil. In another example, the signal may be a difference in texture of the absorbent fibrous structure or a difference in the physical state of the absorbent fibrous structure, for example the absorbent fibrous structure dissolves and/or vaporizes when the absorbent fibrous structure adsorbs soil.

Dispersion or Emulsion

The dispersion or emulsion of the present invention comprises a continuous phase, for example a non-aqueous continuous phase such as a hydrocarbon fluid phase, for example an oil (for example white mineral oil) and/or ester (for example alkyl alkylates, such as octyl stearate) and/or high viscosity oil (about 1000 cP), such as a synthetic oil, phase, and a dispersed phase (discontinuous phase) comprising one or more polymer, for example copolymer, such as branched copolymer soil adsorbing agents, for example in the form of water-soluble soil adsorbing polymer particles present in the continuous phase.

In one example, the dispersion or emulsion of the present invention may comprise 50% or greater by weight of polymer, for example copolymer, such as branched copolymer soil adsorbing agent and 50% or less of a hydrocarbon fluid.

In another example, the dispersion or emulsion of the present invention may be made by diluting a dispersion or emulsion comprising 50% or greater by weight of polymer, for example copolymer, such as branched copolymer soil adsorbing agent and a hydrocarbon fluid with additional hydrocarbon fluid, for example alkyl alkylate and/or a high viscosity oil (about 1000 cP), such as a synthetic oil, to reduce the level of polymer soil adsorbing agent to less than 37% by weight of the dispersion or emulsion.

In another example of the present invention, the dispersion or emulsion comprising greater than 0% but less than 37%, for example less than 35% and/or less than 30%, but greater than 0% and/or greater than 5% and/or greater than 10% and/or greater than 15% and/or greater than 20% and/or greater than 22% and/or from about 22% to about 35%, by weight of the polymer soil adsorbing agent.

In one example, the dispersion or emulsion is a dewatered dispersion or emulsion. The dispersion or emulsion of the present invention may be an inverse dispersion or emulsion and/or a dewatered, inverse dispersion or emulsion. In still another example, the dispersion or emulsion is a non-dewatered dispersion or emulsion and/or a non-dewatered, inverse dispersion or emulsion. In yet another example, the dispersion or emulsion is a partially dewatered dispersion or emulsion and/or a partially dewatered, inverse dispersion or emulsion. In one example, the non-dewatered and/or partially dewatered dispersion or emulsion of the present invention mitigates and/or eliminates the sticky/tacky sensorial feel of the polymer soil adsorbing agent.

In one example, the dispersion or emulsion, for example the dewatered dispersion or emulsion, comprises less than 7% and/or less than 5% and/or less than 3% and/or less than 1% to about 0% by weight of the dispersion or emulsion of water. In another example, at least a portion of any water present in the dewatered dispersion or emulsion is present in at least one of the soil adsorbing polymer particles of the dewatered dispersion or emulsions of the present invention.

In one example, the neat dispersion or emulsion may exhibit a bulk viscosity of less than about 3000 cP and/or less than about 2500 cP and/or less than about 2000 cP and/or less than about 1000 cP and/or less than about 600 cP and/or less than about 300 cP and/or less than about 250 cP and/or less than about 100 cP and/or less than about 60 cP as measured according to the Bulk Viscosity Test Method described herein. In another example, the neat dispersion or emulsion may exhibit a bulk viscosity of greater than about 30 and/or greater than about 50 cP as measured according to the Bulk Viscosity Test Method described herein. In one example, the neat dispersion or emulsion exhibits bulk viscosity of from about 100 cP to about 3000 cP and/or from about 250 cP to about 2500 cP and/or from about 300 cP to about 1500 cP as measured according to the Bulk Viscosity Test Method described herein. The neat dispersion or emulsion may exhibit a bulk viscosity of from about 30 cP to about 50 cP as measured according to the Bulk Viscosity Test Method.

In another example, the dispersion or emulsion as a whole may exhibit a VOC content of less than 5.5% and/or less than 3% and/or less than 1% and/or less than 0.75% as measured according to the VOC Test Method described herein.

In one example, the dispersion or emulsion comprises less than 500 ppm and/or less than 350 ppm and/or less than 200 ppm and/or less than 150 ppm and/or less than 50 ppm and/or no detectable level of residual acrylamide monomer as measured according to the Acrylamide Monomer Test Method described herein.

In one example, the dispersion or emulsion may comprise two or more polymer soil adsorbing agents. In another example, the dewatered dispersion or emulsion may comprise a blend (mixture) of two or more polymer soil adsorbing agents. In yet another example, the dewatered dispersion or emulsion may comprise two or more different polymer soil adsorbing agents.

a. Hydrocarbon Fluid

In one example, the dispersion or emulsion comprises a non-aqueous continuous phase comprising a hydrocarbon fluid. The hydrocarbon fluid may exhibit a VOC content of less than 60% and/or less than 50% and/or less than 40% and/or less than 30% and/or less than 20% and/or less than 10% and/or less than 5% and/or less than 1% as measured according to the VOC Test Method described herein.

In one example, the hydrocarbon fluid comprises an oil, such as a mineral oil, for example white mineral oil, and/or a vegetable oil. Non-limiting examples of suitable oils are selected from the group consisting of: paraffinic oils (such as liquid paraffin, mineral oil, for example white mineral oil (Protol® is a white mineral oil commercially available from Sonneborn Refined Products) and mixtures thereof), naphthenic oils (such as cycloalkanes of the general formula $C_nH_{2(n+1-g)}$ wherein n is the number of carbon atoms, for example greater than 6 and/or greater than 8 and/or greater than 10, and g is the number of rings in the molecule, for example greater than 1 and/or greater than 2 and mixtures of such cycloalkanes).

In another example, the hydrocarbon fluid comprises an ester, such as an alkyl alkylate, for example a $C_4$-$C_{20}$ stearate, for example octyl stearate, and/or $C_4$-$C_{20}$ oleate, for example butyl oleate. Non-limiting examples of other suitable esters are selected from the group consisting of: synthetic ester oils prepared by the reaction of a carboxylic acid and an alcohol of the general formula $CH_3(CH_2)_xCO_2(CH_2)_yCH_3$ wherein x and y are independently from 1 to about 20 and/or from about 6 to about 20; additionally the hydrocarbon chains may be saturated, mono-unsaturated and/or polyunsaturated and exist as a water insoluble oil at 23° C.±1.0° C. In one example, the hydrocarbon fluid comprises an alkyl alkylate selected from the group consisting of the alkyl alkylates in Table 1 below and mixtures thereof.

TABLE 1

| | | |
|---|---|---|
| Butyl oleate | Glycerol monooleate | Octyl stearate |
| Butyl stearate | Glycerol monolaurate | Oleic |
| Cetyl stearyl stearate | Glycerol monostearate | diethanolamide |
| Coconut diethanolamide | Glycerol trioleate | Polyethylene |
| Di-2-ethyl hexyl phthalate | Isooctyl stearate | glycol oleate |
| Di-2-ethyl hexyl sulfosuccinate | Methyl castorate | Potassium cocoate |
| Dicetyl pthalate | Methyl cocoate | Potassium laurate |
| Diethyl stearates | Methyl laurate | Potassium oleate |
| Ethyl castorate | Methyl oleate | Propylene glycol |
| Ethyl cocoate | Methyl ricinoleate | oleate |
| Ethyl laurate | Methyl stearate | Stearyl stearate |
| Ethyl oleate | Methyl tallowate | |
| Ethyl ricinoleate | Myristyl myristate | |
| Ethyl stearate | | |
| Ethylene glycol distearate | | |

Non-limiting examples of other suitable hydrocarbon fluids are selected from the group consisting of: vegetable oil, for example triglycerides such as Safflower, Sunflower, Soybean, Canola, and Rapeseed oils, and mixtures thereof.

The hydrocarbon fluid may be present in the dispersion or emulsion at a level of at least about 10% and/or at about least 25% and/or at least about 30% and/or at least about 40% and/or at least about 50% and/or less than about 90% and/or less than about 80% and/or less than about 70% and/or less than about 60% by weight of the dispersion or emulsion.

In one example, the dispersion or emulsion may comprise an oil, such as white mineral oil, and an ester, such as an alkyl alkylate, for example octyl stearate, and/or a high viscosity oil (about 1000 cP), such as a synthetic oil.

b. Inverting Surfactant

The dispersion or emulsion may comprise an inverting surfactant. In one example, an inverting surfactant is present in the dispersion or emulsion at a level of at least 6% and/or greater than 6% and/or at least 9% and/or at least 12% to about 30% and/or to about 20% and/or to about 15% by weight of the dispersion or emulsion. In another example, the inverting surfactant is present in the dispersion or emulsion at a level of from about 0 to about 15% and/or from about 5 to about 13% by weight of the dispersion or emulsion. The upper limit of the inverting surfactant level is only linked to the stability of the dispersion or emulsion, once the inverting surfactant is added. In one example, 1 to 7% by weight of the dispersion or emulsion of the inverting surface is enough to get a proper inversion in aqueous systems.

The inverting surfactant may improve the polymer's (water-soluble polymer particle polymer) dissolution in water.

In one example, the inverting surfactant comprises a nonionic surfactant. In another example, the inverting surfactant exhibits an HLB of at least 10, and/or from about 10 to 20 and/or from about 10 to about 15 and/or from about 10 to about 14.

In another example, the inverting surfactant is selected from the group consisting of: fatty alcohol ethoxylates for example Plurafac LF400, alkyl polyglucosides, ethoxylated sorbitan esters, for instance ethoxylated sorbitan oleate with 20 mequivalents of ethylene oxide (EO 20), Castor oil ethoxylate (Alkamuls EL-620), 2) Tridecyl alcohol ethoxylate (Alkamuls BC-720), Propylene oxide/ethylene oxide copolymer (ICI RA-290), nonyl phenol ethoxylate (Alkasurf CO-630), and propylene oxide/ethylene oxide copolymer (ICI RA-280). Certain silicone compounds such as dimethicone copolyols may also be used as inverting surfactants.

In one example, a portion of the inverting surfactant present in the dispersion or emulsion may be present in at least one of the water-soluble polymer particles present in the dispersion or emulsion.

In another example, at least a portion and/or a majority and/or substantially all, if not all, of the inverting surfactant present in the dispersion or emulsion is present in the continuous phase (hydrocarbon fluid) of the dispersion or emulsion.

c. Emulsifying Surfactant

The dispersion or emulsion may also comprise an emulsifying surfactant. In one example, an emulsifying surfactant is present in the dispersion or emulsion at a level of at least 1% and/or at least 2% and/or at least 3% and/or at least 4% to about 20% and/or to about 10% and/or to about 6% by weight of the dispersion or emulsion.

In one example, the emulsifying surfactant comprises a nonionic surfactant. In another example, the emulsifying surfactant exhibits an HLB of less than 10 and/or from about 3 to about 8.

In one example the emulsifying surfactant includes sorbitan monooleate and/or sorbitan isostearate. Non-limiting examples of other suitable emulsifying surfactants include those surfactants described in U.S. Pat. No. 6,686,417, for example sorbitan fatty acid esters, such as the mono, sesqui, and/or tri-fatty acid esters, for example $C_{14}$ to $C_{20}$ mono-unsaturated fatty acid like oleic acid, esters and sorbitan mono-oleate; glycerol mono and/or di-fatty acid esters, for example $C_{14}$ to $C_{20}$ mono-unsaturated fatty acid, such as oleic acid, esters; and fatty acid alkanolamides, for example those ethanolamides, such as diethanolamides, for example those diethanolamides based on $C_{14}$ to $C_{20}$ mono-unsaturated fatty acids, such as oleic acid. The oleic acid in such compounds may be provided by mixed fatty acid feedstocks e.g. rape seed fatty acids, including $C_{14}$ to $C_{20}$ mono-unsaturated fatty acid, particularly oleic acid, as a main constituent. In one example, the emulsifying surfactants include those commercially available from ICI Surfactant under the trade name Span 80. Additional non-limiting examples of emulsifying surfactants include ethylene oxide propylene oxide block copolymers, alkylene (generally ethylene) oxide condensates of alkyl phenols or fatty alcohols, and polyalkylene (generally ethylene) glycol condensates of fatty acids. Suitable materials are ethylene oxide condensates of octyl phenol or nonyl phenol, ethylene oxide condensates of fatty alcohols such as blends of cetyl and oleyl alcohol or C9-11 alkyl alcohols, polyethylene glycol 200, 300 or 400 oleates of the isopropylamine salt of dodecyl benzene sulphonate.

In one example, the emulsifying surfactant is associated with, for example present in and/or present on, the polymer soil adsorbing agent, for example the water-soluble soil adsorbing polymer particle, to keep the polymer soil adsorbing agent, such as the water-soluble polymer particle, dispersed within the continuous phase, for example the hydrocarbon fluid within the dispersion or emulsion of the present invention.

In one example, at least a portion and/or a majority and/or substantially all, if not all, of the emulsifying surfactant present in the dispersion or emulsion is present in and/or on at least one of the water-soluble soil adsorbing polymer particles within the dispersion or emulsion.

In another example, a portion of the emulsifying surfactant present in the dispersion or emulsion may be present in the continuous phase (hydrocarbon fluid) of the dispersion or emulsion.

d. Water-Soluble Polymer Particles

One or more water-soluble polymer particles, such as water-soluble copolymer particles, for example water-soluble soil adsorbing branched copolymer particles, may be dispersed within the continuous phase (hydrocarbon fluid) of the dispersion or emulsion.

In one example, the water-soluble polymer particles are present in the dispersion or emulsion at a level of greater than 10% and/or greater than 15% and/or greater than 20% and/or greater than 30% and/or greater than 50% by weight of the dispersion or emulsion.

In one example, the water-soluble polymer particles, such as water-soluble copolymer particles, for example water-soluble soil adsorbing branched copolymer particles, are in and/or on the absorbent fibrous structure at a level of greater than 0.005% and/or greater than 0.0075% and/or greater than 0.01% and/or greater than 0.05% and/or greater than 0.1% and/or greater than 0.15% and/or greater than 0.2% and/or less than 5% and/or less than 3% and/or less than 2% and/or less than 1% by weight of the absorbent fibrous structure. In one example, the water-soluble polymer particle is present in and/or on the absorbent fibrous structure at a level of from about 0.005% to about 1% by weight of the absorbent fibrous structure.

In another example of the present invention, the absorbent fibrous structure may comprise the water-soluble polymer particles, such as water-soluble copolymer particles, for example water-soluble soil adsorbing branched copolymer particles, at a level of from greater than 0 pounds/ton (#/ton) and/or greater than 0.1#/ton and/or greater than 0.5#/ton and/or greater than 1#/ton and/or greater than 2#/ton and/or greater than 3#/ton and/or to less than 20#/ton and/or to less than 15#/ton and/or to less than 10#/ton and/or to less than 6#/ton and/or to 5 #/ton or less and/or to 4#/ton or less by weight of the absorbent fibrous structure.

The level of water-soluble polymer particles, such as water-soluble copolymer particles, for example as water-soluble soil adsorbing branched copolymer particles, present in and/or on an absorbent fibrous structure as used herein according to the present invention is in terms of active solids basis of the soil adsorbing polymer.

In one example, the water-soluble polymer particles, when present on an absorbent fibrous structure of the present invention, are non-aqueous and/or dry and/or void of water (for example less than 10% and/or less than 7% and/or less than 5% and/or less than 3% to 0 or about 0% by weight of the water-soluble polymer particle). This clearly distinguishes the water-soluble polymer particles from latex, which is an aqueous emulsion of polymers.

One or more of the water-soluble polymer particles of the present invention comprises a water-soluble soil adsorbing copolymer, such as a water-soluble soil adsorbing branched copolymer. Without wishing to be bound by theory, it is believed that the water-soluble polymer, for example the water-soluble soil adsorbing branched copolymer, present on an absorbent fibrous structure of the present invention is in a coiled configuration until exposed to excess polar solvent, for example water, at which time it uncoils to an extended functional form to provide its benefits, for example soil adsorbing benefits.

In one example, the water-soluble polymer particle, such as water-soluble copolymer particles, for example water-soluble soil adsorbing branched copolymer particle, comprises the water-soluble soil adsorbing copolymer, such as a water-soluble soil adsorbing branched copolymer, and an emulsifying surfactant.

In one example, the water-soluble polymer particle exhibits an average particle size of from about 500 nm to about 50 μm and/or from about 700 nm to about 25 μm and/or from about 800 nm to about 10 μm and/or from about 800 nm to about 5 μm and/or from about 800 nm to about 1 μm.

e. Polymer (Copolymer and/or Branched Copolymer) Soil Adsorbing Agent

A polymer soil adsorbing agent as described herein provides enhanced benefits in capturing soil. Such polymer soil adsorbing agents can be used singularly or in combination with other components to form a cleansing solution. Such polymer soil adsorbing agent can include several monomeric units thus it can be referred to as a copolymer rather than a homopolymer, which consists of a single type of monomeric unit. The polymer soil adsorbing agent of the present invention may be a terpolymer (3 different monomeric units). The polymer of the present invention may be a random copolymer. In one example, a polymer of the present invention may be water-soluble and/or water-dispersible, which means that the polymer does not, over at least a certain pH and concentration range, form a two-phase composition in water at 23° C.±2.2° C. and a relative humidity of 50%±10%.

In one example, the polymer soil adsorbing agent, for example copolymer, such as a branched copolymer soil adsorbing agent exhibits a weight average molecular weight of greater than 750,000 and/or greater than 1,500,000 and/or greater than 4,000,000 and/or to about 40,000,000 and/or to about 20,000,000 and/or to about 10,000,000.

In another example, the polymer soil adsorbing agent, for example copolymer, such as a branched copolymer soil adsorbing agent exhibits a number average molecular weight of greater than 200,000 g/mol and/or greater than 500,000 g/mol and/or greater than 750,000 g/mol and/or greater than 900,000 g/mol to less than 2,000,000 g/mol and/or less than 1,750,000 g/mol and/or less than 1,500,000 g/mol. In one example, the polymer soil adsorbing agent exhibits a number average molecular weight of from about 500,000 g/mol to about 2,000,000 g/mol and/or from about 900,000 g/mol to about 1,700,000 g/mol.

In yet another example, the polymer soil adsorbing agents of the present invention exhibit a Number Average Molecular Weight of less than 2,000,000 g/mol and/or less than 1,750,000 g/mol and/or less than 1,700,000 g/mol and/or less than 1,500,000 g/mol and/or greater than 500,000 g/mol and/or greater than 900,000 g/mol. In another example, the polymer soil adsorbing agents of the present invention exhibit a Number Average Molecular Weight of from about 500,000 to 2,000,000 g/mol and/or from about 900,000 to 1,700,000 g/mol.

In one example, the polymer soil adsorbing agents, for example copolymer, such as a branched copolymer soil adsorbing agent of the present invention may exhibit a Soil Adsorption Value of at least 38 mg and/or at least 40 mg and/or at least 42 mg and/or at least 45 mg and/or at least 47 mg and/or at least 50 mg and/or at least 53 mg and/or at least 55 mg and/or at least 57 mg and/or at least 60 mg and/or at least 62 mg as measured according to the Soil Adsorption Test Method described herein.

Non-limiting examples of polymer soil adsorbing agents of the present invention, for example copolymer soil adsorbing agents, such as branched copolymer soil adsorbing agents, comprise monomeric units derived from acrylic acid and/or quaternary ammonium compounds and/or acrylamide.

In one example, the polymer soil adsorbing agent, for example copolymer, such as a branched copolymer soil adsorbing agent may be used as a highly concentrated inverse dispersion or emulsion (for example a water-in-oil dispersion or emulsion), containing greater than 10% and/or greater than 15% and/or greater than 20% and/or greater than 25% and/or greater than 30% and/or greater than 35% and/or to about 60% and/or to about 55% and/or to about 50% and/or to about 45% active. The oil (hydrocarbon fluid) phase may consist of high quality mineral oil, such as white mineral oil, and/or an alkyl alkylate, such as octyl stearate, and/or a high viscosity (about 1000 cP) synthetic oil. In another example the soil adsorbing agents may be used as a highly concentrated dewatered dispersion or emulsion for example dry particles suspended in a continuous hydrocarbon phase, containing greater than 10% and/or greater than 15% and/or greater than 20% and/or greater than 25% and/or greater than 30% and/or greater than 35% and/or to about 60% and/or to about 55% and/or to about 50% and/or to about 45% active. In one example, the oil phase may consist of high quality mineral oil with boiling point range of 468-529° F. or a heavy mineral oil with boiling point range of 608-968° F. In one example, the soil adsorbing agent may be used as a highly concentrated inverse emulsion wherein the continuous phase of the inverse dispersion or emulsion comprises mineral oil, such as white mineral oil.

The dispersion or emulsions, for example inverse dispersions or emulsions, such as dewatered inverse dispersions or emulsions, of the present invention may be directly applied to a surface of an absorbent fibrous structure, a surface of a wet absorbent fibrous structure and/or added to the wet-end of a papermaking process.

The polymer soil adsorbing agents, for example copolymer, such as branched copolymer soil adsorbing agents may be anionic, neutral and/or cationic under pH 4.5 conditions. In one example, the polymer soil adsorbing agents, such as water-soluble copolymer particles, for example the branched copolymer soil adsorbing agent comprises a quaternary ammonium compound under pH 4.5 conditions. In another example, the polymer soil adsorbing agents, such as water-soluble copolymer particles, for example the branched copolymer soil adsorbing agent comprises an amine under pH 4.5 conditions. In still another example, the polymer soil adsorbing agents, such as water-soluble copolymer particles, for example the branched copolymer soil adsorbing agent comprises an acrylamide under pH 4.5 conditions.

The polymer soil adsorbing agent, for example copolymer, such as a branched copolymer soil adsorbing agent may comprise a copolymer, for example a polymer comprising one or more monomeric units derived from quaternary ammonium compounds, amine compounds, acrylamide compounds, acrylic acid compounds and mixtures thereof at various weight ratios within the polymer.

In one example, polymer soil adsorbing agent is a copolymer of acrylamide and one or more other nonionic monomers, for example non-acrylamide monomers, such as hydroxyalkylacrylate, for example hydroxypropylacrylate, In one example, the polymer is a branched copolymer soil adsorbing agent is a polymer of acrylamide and methylene bis acrylamide, a crosslinking agent, that converts a typical linear polyacrylamide into a branched structure. The methylene bis acrylamide may be present in the branched copolymer at a level of less than 200 ppm and/or less than 100 ppm and/or less than 50 ppm and/or greater than 1 ppm and/or greater than 2 ppm and/or greater than 10 ppm and/or greater than 20 ppm. In one example, the methylene bis acrylamide may be present in the branched copolymer at a level of from about 2.5 ppm to about 25 ppm.

In another example, the polymer soil adsorbing agent is a copolymer of a monomeric unit derived from an acrylamide compound and a monomeric unit derived from a hydroxyalkylacrylate compound, such as hydroxypropylacrylate. The monomeric unit derived from the hydroxyalkylacrylate compound may be present in the copolymer at a level of less than 50% and/or less than 40% and/or less than 30% and/or less than 20% and/or less than 10% and/or less than 5% and/or greater than 0.01% and/or greater than 0.1% and/or greater than 0.5%. In one example, the hydroxyalkylacrylate may be present in the copolymer at a level of from about 1% to about 3%.

The polymer soil adsorbing agent, for example copolymer, such as a branched copolymer soil adsorbing agent of the present invention may be present in the form of one or more water-soluble polymer particles of the present invention.

The soil adsorbing polymer of the present invention may comprise a one or more monomeric units, such as nonionic monomeric units, such as a nonionic monomeric unit derived from an acrylamide compound. Non-limiting examples of suitable nonionic monomeric units include nonionic monomeric units derived from nonionic monomers selected from the group consisting of: hydroxyalkyl esters of α,β-ethylenically unsaturated acids, such as hydroxyethyl or hydroxypropyl acrylates and methacrylates, glyceryl monomethacrylate, α,β-ethylenically unsaturated amides such as acrylamide, N,N-dimethylmethacrylamide, N-methylolacrylamide, α,β-ethylenically unsaturated monomers bearing a water-soluble polyoxyalkylene segment of the poly(ethylene oxide) type, such as poly(ethylene oxide) α-methacrylates (Bisomer S20W, S10W, etc., from Laporte) or α,ω-dimethacrylates, Sipomer BEM from Rhodia (ω-behenyl polyoxyethylene methacrylate), Sipomer SEM-25 from Rhodia (ω-tristyrylphenyl polyoxyethylene methacrylate), α,β-ethylenically unsaturated monomers which are precursors of hydrophilic units or segments, such as vinyl acetate, which, once polymerized, can be hydrolyzed in order to give rise to vinyl alcohol units or polyvinyl alcohol segments, vinylpyrrolidones, α,β-ethylenically unsaturated monomers of the ureido type, and in particular 2-imidazolidinone-ethyl methacrylamide (Sipomer WAM II from Rhodia). Other nonionic monomeric units suitable for the present invention include nonionic monomeric units derived from nonionic monomers selected from the group consisting of: vinylaromatic monomers such as styrene, alpha-methylstyrene, vinyltoluene, vinyl halides or vinylidene halides, such as vinyl chloride, vinylidene chloride, $C_1$-$C_{12}$ alkylesters of α,β-monoethylenically unsaturated acids such as methyl, ethyl or butyl acrylates and methacrylates, 2-ethylhexyl acrylate, vinyl esters or allyl esters of saturated carboxylic acids, such as vinyl or allyl acetates, propionates, versatates, stearates, α,β-monoethylenically unsaturated nitriles containing from 3 to 12 carbon atoms, such as acrylonitrile, methacrylonitrile, α-olefins such as ethylene, conjugated dienes, such as butadiene, isoprene, chloroprene.

The soil adsorbing polymer of the present invention may comprise an anionic monomeric unit, such as an anionic monomeric unit derived from acrylic acid. Non-limiting examples of anionic monomeric units suitable for the present invention include anionic monomeric units derived from anionic monomers selected from the group consisting of: monomers having at least one carboxylic function, for instance α,β-ethylenically unsaturated carboxylic acids or the corresponding anhydrides, such as acrylic, methacrylic or maleic acids or anhydrides, fumaric acid, itaconic acid, N-methacroylalanine, N-acryloylglycine, and their water-soluble salts, monomers that are precursors of carboxylate functions, such as tert-butyl acrylate, which, after polymerization, give rise to carboxylic functions by hydrolysis, monomers having at least one sulfate or sulfonate function, such as 2-sulfooxyethyl methacrylate, vinylbenzene sulfonic acid, allyl sulfonic acid, 2-acrylamido-2-methylpropane sulfonic acid (AMPS), sulfoethyl acrylate or methacrylate, sulfopropyl acrylate or methacrylate, and their water-soluble salts, monomers having at least one phosphonate or phosphate function, such as vinylphosphonic acid, etc., the esters of ethylenically unsaturated phosphates, such as the phosphates derived from hydroxyethyl methacrylate (Empicryl 6835 from Rhodia) and those derived from polyoxyalkylene methacrylates, and their water-soluble salts, and 2-carboxyethyl acrylate (CEA).

In one example, the soil adsorbing polymer comprises a nonionic monomeric unit derived from an acrylamide compound and an anionic monomeric unit derived from acrylic acid.

The soil adsorbing polymer of the present invention may comprise a cationic monomeric unit, such as a cationic monomeric unit derived from cationic monomers selected from the group consisting of: N,N-(dialkylamino-ω-alkyl) amides of α,β-monoethylenically unsaturated carboxylic acids, such as N,N-dimethylaminomethylacrylamide or -methacrylamide, 2-(N,N-dimethylamino)ethylacrylamide or -methacrylamide, 3-(N,N-dimethylamino)propylacrylamide or -methacrylamide, and 4-(N,N-dimethylamino)butylacrylamide or -methacrylamide, α,β-monoethylenically unsaturated amino esters such as 2-(dimethylamino)ethyl acrylate (DMAA), 2-(dimethylamino)ethyl methacrylate (DMAM), 3-(dimethylamino)propyl methacrylate, 2-(tert-butylamino)ethyl methacrylate, 2-(dipentylamino)ethyl methacrylate, and 2(diethylamino)ethyl methacrylate, vinylpyridines, vinylamine, vinylimidazolines, monomers that are precursors of amine functions such as N-vinylformamide, N-vinylacetamide, which give rise to primary amine functions by simple acid or base hydrolysis, acryloyl- or acryloyloxyammonium monomers such as trimethylammonium propyl methacrylate chloride, trimethylammonium ethylacrylamide or -methacrylamide chloride or bromide, trimethylammonium butylacrylamide or -methacrylamide methyl sulfate, trimethylammonium propylmethacrylamide methyl sulfate, (3-methacrylamidopropyl)trimethylammonium chloride (MAPTAC), (3-methacrylamidopropyl)trimethylammonium methyl sulphate (MAPTA-MES), (3-acrylamidopropyl)trimethylammonium chloride (APTAC), methacryloyloxyethyl-trimethylammonium chloride or methyl sulfate, and acryloyloxyethyltrimethylammonium chloride; 1-ethyl-2-vinylpyridinium or 1-ethyl-4-vinylpyridinium bromide, chloride or methyl sulfate; N,N-dialkyl-diallylamine monomers such as N,N-dimethyldiallylammonium chloride (DADMAC); polyquaternary monomers such as dimethylaminopropylmethacrylamide chloride and N-(3-chloro-2-hydroxypropyl)trimethylammonium (DIQUAT) and 2-hydroxy-$N^1$-(3-(2((3-methacrylamidopropyl)dimethylammino)-acetamido)propyl)-$N^1$, $N^1$, $N^3$, $N^3$, $N^3$-pentamethylpropane-1,3-diaminium chloride (TRIQUAT), and. In one example, the cationic monomeric unit comprises a quaternary ammonium monomeric unit, for example a monoquaternary ammonium monomeric unit, a diquaternary ammonium monomeric unit or a triquaternary monomeric unit. In one example, the cationic monomeric unit is derived from MAPTAC. In another example, the cationic monomeric unit is derived from DADMAC. In still another example, the cationic monomeric unit is derived from 2-hydroxy-$N^1$-(3-(2((3-methacrylamidopropyl)dimethylammino)-acetamido)propyl)-$N^1$, $N^1$, $N^3$, N3, $N^3$-pentamethyl-propane-1,3-diaminium chloride.

f. Optional Additives.

Optional additives may be added to the dispersion or emulsion of the present invention. For example, sodium bisulfite may be added to the dispersion or emulsion after completion of polymerization of the water-soluble polymer particle, for example water-soluble soil adsorbing polymer particle, to aid in the reduction of residual acrylamide monomer that may be present in the neat emulsion. One can also utilize anionic dispersants, for example a carboxylic acid, to aid in maintaining stability of the dispersion or emulsion.

In one example, the soil adsorbing copolymer exhibits a charge density as measured according to the Charge Density Test Method described herein. In another example, the polymer soil adsorbing agent exhibits a net charge density of greater than −5 meq/g to less than 5 meq/g and/or from greater than −5 meq/g to about −0.1 meq/g as measured according to the Charge Density Test Method described herein. In another example, the polymer soil adsorbing agent exhibits a net charge density of greater than 0 and/or greater than 1 and/or greater than 2 and/or greater than 4 and/or greater than 6 and/or to less than about 10 and/or to about 8 meq/g as measured according to the Charge Density Test Method described herein.

In one example, the soil adsorbing polymer of the present invention exhibits a UL Viscosity of from about 1 to about 6 cP as measured according to the UL Viscosity Test Method described herein.

The soil adsorbing polymer may be present in the dispersion or emulsion at a level of greater than 10% and/or greater than 25% and/or greater than 30% and/or greater than 40% and/or greater than 50% and/or to about 90% and/or to about 75% and/or to about 65% by weight of the dispersion or emulsion. In one example, the soil adsorbing polymer is present in the dispersion or emulsion at a level of from about 30% to about 75% and/or from about 40% to 65% by weight of the dispersion or emulsion.

In one example, the soil adsorbing polymer is present in and/or on the absorbent fibrous structure at a level of greater than 0.005% by weight of the absorbent fibrous structure. In another example, the soil adsorbing polymer is present in the absorbent fibrous structure at a level of from about 0.005% to about 5% and/or from about 0.005% to about 3% by weight of the absorbent fibrous structure.

Non-Limiting Synthesis Example—Process for Making a Dispersion or Emulsion

The dispersion or emulsions of the present invention may be made by any suitable process known in the art. A non-limiting example of a suitable process follows.

First, an inverse dispersion or emulsion is prepared by dispersing a non-continuous phase (discontinuous phase), such as an aqueous phase, in a continuous phase, such as a non-aqueous continuous phase, for example a hydrocarbon fluid phase, such as an oil phase and/or an ester phase as follows. The aqueous phase is prepared by mixing one or more water-soluble, ethylenically unsaturated addition polymerizable monomers such as acrylamide and/or acrylic acid, and optionally, a water-soluble salt, such as alkali salts such as sodium chloride, sodium bromide, lithium chloride, lithium bromide, in water. When present, the water-soluble salt may be present in the dewatered dispersion or emulsion at a level of from about 0% to about 4% and/or from about 0.05% to about 2% by weight of the dewatered dispersion or emulsion. The hydrocarbon fluid phase is prepared by mixing an emulsifying surfactant and an inverting surfactant in a hydrocarbon fluid, such as an oil, for example white mineral oil, that exhibits a VOC content of less than 60% as measured according to the VOC Test Method described herein.

Next, a free radical initiator is added to either the aqueous phase or the oil phase depending upon the solubility characteristics of the initiator.

The aqueous phase (discontinuous phase) is then dispersed into the hydrocarbon fluid phase (continuous phase). The water-soluble monomers are then polymerized within the aqueous phase thus resulting in an inverse emulsion comprising a water-soluble polymer, for example a water-soluble soil adsorbing polymer.

The inverse dispersion or emulsion (water-in-oil dispersion or emulsion) may then be dehydrated to less than 7% and/or less than 5% and/or less than 3% and/or less than 1% to about 0% by weight of the dispersion or emulsion of water, for example by azeotropic distillation, to produce a dewatered dispersion or emulsion (dewatered inverse dispersion or emulsion) of the present invention comprising a plurality of water-soluble polymer particles dispersed throughout the oil (hydrocarbon fluid) continuous phase.

Process for Making Absorbent Fibrous Structure

An absorbent fibrous structure suitable for use in the present invention may be made by any suitable process known in the art.

In order to make the absorbent fibrous structure comprising a polymer soil adsorbing agent, for example a water-soluble soil adsorbing polymer particle, the fibrous structure is contacted with the polymer soil adsorbing agent, in any of the forms described herein for example, of the present invention.

In another example, a process for making an absorbent fibrous structure, such as a wet-laid fibrous structure, comprising a polymer soil adsorbing agent of the present invention comprises the steps of:
a. providing a fiber slurry;
b. depositing the fiber slurry onto a foraminous wire to form an embryonic web;
c. drying the embryonic web, for example at least partially on a patterned belt, to produce a fibrous structure; and
d. contacting the fibrous structure with a polymeric fluid comprising a polymer soil adsorbing agent, in any of the forms described herein for example, of the present invention to produce an absorbent fibrous structure, for example a dry fibrous structure, comprising a polymer soil adsorbing agent of the present invention.

In yet another example, a process for making an absorbent fibrous structure, such as a wet-laid fibrous structure, comprises the steps of:
a. providing a fiber slurry;
b. adding a polymer soil adsorbing agent, such as a copolymer, for example a branched copolymer soil adsorbing agent, for example a water-soluble soil adsorbing polymer, in any form described herein for example, to the fiber slurry, for example after a dispersion or emulsion comprising a polymer soil adsorbing agent is inverted into an aqueous dispersion or emulsion (for example by utilizing procedures as outlined by the supplier of the dispersion or emulsion);
c. depositing the fiber slurry onto a foraminous wire to form an embryonic web; and
d. drying the embryonic web, for example at least partially on a patterned belt; and e. contacting the absorbent fibrous structure with a polymeric fluid comprising a polymer soil adsorbing agent in any form described herein for example, of the present invention to produce an absorbent fibrous structure, for example a dry fibrous structure, comprising a polymer soil adsorbing agent of the present invention.

The fiber slurries and/or absorbent fibrous structures may comprise permanent and/or temporary wet strength agents such as Kymene® (permanent wet strength) and Hercobond® (temporary wet strength) both available from Ashland Inc. and/or Parez® (wet strength chemistries) available from Kemira Chemicals, Inc.

The fiber slurries and/or absorbent fibrous structures may comprise dry strength agents such as carboxymethylcellulose, starch, polyvinylamides, polyethyleneimines, melamine/formaldehyde, epoxide, and mixtures thereof.

In still yet another example, a process for making an absorbent fibrous structure, such as an air-laid fibrous structure, comprises the steps of:
a. providing pulp fibers;
b. producing an air-laid fibrous structure from the pulp fibers; and
c. optionally applying a binder, for example a latex binder, to a surface of the air-laid fibrous structure; and
d. contacting the air-laid fibrous structure with a polymeric fluid comprising a polymer soil adsorbing agent, in any form described herein for example, of the present invention to produce an absorbent fibrous structure comprising a polymer soil adsorbing agent of the present invention.

In one example, the polymer soil adsorbing agent, in any form described herein for example, of the present invention may be added to an absorbent fibrous structure during papermaking, between the Yankee dryer and the reel, and/or during converting by applying it to one or more surfaces of the fibrous structure. In one example, a single-ply paper towel comprises the soil adsorbing agent of the present invention on one surface of the paper towel. In another example, a single-ply paper towel comprises the soil adsorbing agent of the present invention on both surfaces of the paper towel. In still another example, a two-ply paper towel comprises the soil adsorbing agent, in any form described herein for example, of the present invention on one or both exterior surfaces of the two-ply paper towel. In still another example, a two-ply paper towel comprises the soil adsorbing agent of the present invention on one or more interior surfaces of the two-ply paper towel. In yet another example, a two-ply paper towel comprises the soil adsorbing agent of the present invention on one or more exterior surfaces and one or more interior surfaces of the two-ply paper towel. One of ordinary skill would understand that one or more exterior surfaces and one or more interior surfaces of a three or more ply paper towel could comprise the soil adsorbing agent of the present invention.

In another example, the absorbent fibrous structure comprising a polymeric fluid comprising a polymer soil adsorbing agent, in any form described herein for example, of the present invention may be made by printing a soil adsorbing agent, in any form described herein for example, onto a surface of an absorbent fibrous structure, for example in a converting operation. The printing operation may occur by any suitable printing equipment, for example by way of a gravure roll and/or by a permeable fluid applicator roll. In still another example, an absorbent fibrous structure comprising a polymer soil adsorbing agent of the present invention may be made by extruding a polymer soil adsorbing agent, in any form described herein for example, onto a surface of an absorbent fibrous structure.

In even another example, an absorbent fibrous structure comprising a polymeric fluid comprising a polymer soil adsorbing agent, in any form described herein for example, of the present invention may be made by spraying a polymer soil adsorbing agent, in any form for example, onto a surface of an absorbent fibrous structure. In yet another example, an absorbent fibrous structure comprising a polymeric fluid comprising a polymer soil adsorbing agent, in any form described herein for example, of the present invention may be made by spraying a polymer soil adsorbing agent, in any form described herein for example, onto a wet fibrous structure during papermaking after the vacuum dewatering step, but before the pre-dryers and/or after the pre-dryers, but before the Yankee.

In even yet another example, an absorbent fibrous structure comprising a polymeric fluid comprising a polymer soil adsorbing agent, in any form described herein for example, of the present invention may be made by depositing a plurality of fibers mixed with a polymer soil adsorbing agent, in any form described herein for example, of the present invention in an air-laid and/or coform process.

In still another example, an absorbent fibrous structure comprising a polymeric fluid comprising a polymer soil adsorbing agent, in any form described herein for example, of the present invention may be made by adding one or more polymer soil adsorbing agents, in any form described herein for example, of the present invention at acceptable locations within spunbonding, meltblowing, dry spinning, carding, and/or hydroentangling processes.

The polymer soil adsorbing agent, in any form described herein for example, of the present invention may be applied to and/or included in an absorbent fibrous structure, in a pattern, such as a non-random, repeating pattern.

NON-LIMITING EXAMPLES

Examples of absorbent fibrous structures; namely, paper towels for use in the comparative and inventive examples below are produced utilizing a cellulosic pulp fiber furnish consisting of about 55% refined softwood furnish consisting of about 44% Northern Bleached Softwood Kraft (Bowater), 44% Northern Bleached Softwood Kraft (Celgar) and 12% Southern Bleached Softwood Kraft (Alabama River Softwood, Weyerhaeuser); about 30% of unrefined hardwood Eucalyptus Bleached Kraft consisting of about 80% (Fibria) and 20% NBHK (Aspen) (Peace River); and about 15% of an unrefined furnish consisting of a blend of about 27% Northern Bleached Softwood Kraft (Bowater), 27% Northern Bleached Softwood Kraft (Celgar), 42% Eucalyptus Bleached Kraft (Fibria) and 4% Southern Bleached Kraft (Alabama River Softwood, Weyerhaeuser). The 55% refined softwood is refined as needed to maintain target wet burst at the reel. Any furnish preparation and refining methodology common to the papermaking industry can be utilized.

A 3% active solution Kymene 5221 is added to the refined softwood line prior to an in-line static mixer and 1% active solution of Wickit 1285, an ethoxylated fatty alcohol available from Ashland Inc. is added to the unrefined Eucalyptus Bleached Kraft (Fibria) hardwood furnish. The addition levels are 21 and 1 lbs active/ton of paper, respectively.

The refined softwood and unrefined hardwood and unrefined NBSK/SSK/Eucalyptus bleached kraft/NDHK thick stocks are then blended into a single thick stock line followed by addition of 1% active carboxymethylcellulose (CMC-Finnfix) solution at 7 lbs active/ton of paper towel, and optionally, a softening agent may be added.

The thick stock is then diluted with white water at the inlet of a fan pump to a consistency of about 0.15% based on total weight of softwood, hardwood and simulated broke fiber. The diluted fiber slurry is directed to a non layered configuration headbox such that the wet web formed onto a Fourdrinier wire (foraminous wire). Optionally, a fines retention/drainage aid may be added to the outlet of the fan pump.

Dewatering occurs through the Fourdrinier wire and is assisted by deflector and vacuum boxes. The Fourdrinier wire is of a 5-shed, satin weave configuration having 87 machine-direction and 76 cross-direction monofilaments per inch, respectively. The speed of the Fourdrinier wire is about 750 fpm (feet per minute).

The embryonic wet web is transferred from the Fourdrinier wire at a fiber consistency of about 24% at the point of transfer, to a belt, such as a patterned belt through-air-drying resin carrying fabric. In the present case, the speed of the patterned through-air-drying fabric is approximately the same as the speed of the Fourdrinier wire. In another case, the embryonic wet web may be transferred to a patterned belt and/or fabric that is traveling slower, for example about 20% slower than the speed of the Fourdrinier wire (for example a wet molding process).

Further de-watering is accomplished by vacuum assisted drainage until the web has a fiber consistency of about 30%.

While remaining in contact with the patterned belt, the web is pre-dried by air blow-through pre-dryers to a fiber consistency of about 65% by weight.

After the pre-dryers, the semi-dry web is transferred to a Yankee dryer and adhered to the surface of the Yankee dryer with a sprayed creping adhesive. The creping adhesive is an aqueous dispersion with the actives consisting of about 75% polyvinyl alcohol, and about 25% CREPETROL® R6390. Optionally a crepe aid consisting of CREPETROL® A3025 may be applied. CREPETROL® R6390 and CREPETROL® A3025 are commercially available from Ashland Inc. (formerly Hercules Inc.). The creping adhesive diluted to about 0.15% adhesive solids and delivered to the Yankee surface at a rate of about 2# adhesive solids based on the dry weight of the web. The fiber consistency is increased to about 97% before the web is dry creped from the Yankee with a doctor blade.

In the present case, the doctor blade has a bevel angle of about 45° and is positioned with respect to the Yankee dryer to provide an impact angle of about 101° and the reel is run at a speed that is about 15% faster than the speed of the Yankee. In another case, the doctor blade may have a bevel angle of about 25° and be positioned with respect to the Yankee dryer to provide an impact angle of about 81° and the reel is run at a speed that is about 10% slower than the speed of the Yankee. The Yankee dryer is operated at a temperature of about 177° C. and a speed of about 800 fpm. The fibrous structure is wound in a roll using a surface driven reel drum having a surface speed of about 656 feet per minute.

The fibrous structure may be subsequently converted into a two-ply paper towel product (an article of manufacture) having a basis weight of about 45 to 54 g/m$^2$.

Example 1

An example of a dispersion or emulsion, for example a dewatered inverse dispersion or emulsion, of the present invention (about 50% polyacrylamide-hydroxypropylacrylate (HPA) (1% hydroxypropylacrylate) copolymer (soil adsorbing agent), about 40% an alkyl alkylate, for example octyl stearate, (hydrocarbon fluid) and about 10% emulsifying and/or inverting surfactants) with the copolymer polyacrylamide-HPA being in the form of micron size highly coiled particles dispersed in the hydrocarbon fluid is applied directly to a surface of the two-ply paper towel product in the converting operation via an extruder.

The fibrous structure plies and/or two-ply paper towel product may be embossed prior to and/or subsequent to the application of the dispersion or emulsion.

Example 2

An example of a dispersion or emulsion, for example a dewatered dispersion or emulsion, of the present invention (about 25% polyacrylamide-hydroxypropylacrylate (HPA) (1% hydroxypropylacrylate) copolymer (soil adsorbing agent), about 65% hydrocarbon fluid (alkyl alkylate, for example octyl stearate) and about 10% emulsifying and/or inverting surfactants) with the copolymer polyacrylamide-HPA being in the form of micron size highly coiled particles dispersed in the hydrocarbon fluid is applied directly to a surface of the two-ply paper towel product in the converting operation via an extruder.

The fibrous structure plies and/or two-ply paper towel product may be embossed prior to and/or subsequent to the application of the dispersion or emulsion.

Example 3

An example of a dispersion or emulsion, for example a dewatered inverse dispersion or emulsion, of the present invention (about 50% polyacrylamide-bismethylenepolyacrylamide (BMA) (25 ppm BMA) branched copolymer (soil adsorbing agent), about 40% an alkyl alkylate, for example octyl stearate, (hydrocarbon fluid) and about 10% emulsifying and/or inverting surfactants) with the branched copolymer polyacrylamide-BMA being in the form of micron size highly coiled particles dispersed in the hydrocarbon fluid is applied directly to a surface of the two-ply paper towel product in the converting operation via an extruder.

The fibrous structure plies and/or two-ply paper towel product may be embossed prior to and/or subsequent to the application of the dispersion or emulsion.

Example 4

An example of a dispersion or emulsiondispersion, for example a dewatered dispersion or emulsion, of the present invention (about 25% polyacrylamide-bismethylenepolyacrylamide (BMA) (25 ppm BMA) branched copolymer (soil adsorbing agent), about 65% hydrocarbon fluid (alkyl alkylate, for example octyl stearate) and about 10% emulsifying and/or inverting surfactants) with the branched copolymer polyacrylamide-BMA being in the form of micron size highly coiled particles dispersed in the hydrocarbon fluid is applied directly to a surface of the two-ply paper towel product in the converting operation via an extruder.

The fibrous structure plies and/or two-ply paper towel product may be embossed prior to and/or subsequent to the application of the dispersion or emulsion.

Example 5

An example of an aqueous hydroxypropylacrylate-polyacrylamide copolymer soil adsorbing agent according to the present invention is made conventional free-radical solution polymerization of acrylamide and hydroxypropylacrylate monomers in water. The resulting aqueous polymer solution can then be used as a polymer soil adsorbing agent solution of the present invention by applying it to a surface of a fibrous structure and/or multi-ply fibrous structure, such as a paper towel or two-ply paper towel, such as via spraying, slot extruding, printing, and/or other suitable known application methods. The fibrous structure plies and/or two-ply paper towel product may be embossed prior to and/or subsequent to the application of the soil adsorbing agent solution.

Example 6

Conventional dispersions or emulsions of hydroxypropylacrylate-polyacrylamide copolymer are prepared by conventional free-radical inverse emulsion polymerization of acrylamide and hydropropylacrylate monomers in oil containing surfactants and dispersions, etc. The resulting fluid contains a dispersion or emulsion of stabilized polymer soil adsorbing particles in oil and water (greater than 7%) mixture. The resulting fluid can then be used as a polymer soil adsorbing agent of the present invention by applying it to a surface of a fibrous structure and/or multi-ply fibrous structure, such as a paper towel or two-ply paper towel, such as via spraying, slot extruding, printing, and/or other suitable known application methods. The fibrous structure plies and/or two-ply paper towel product may be embossed prior to and/or subsequent to the application of the polymer soil adsorbing agent.

Example 7

Dewatered dispersions or emulsions of hydroxypropylacrylate-polyacrylamide copolymer are prepared by conventional free-radical inverse emulsion polymerization of acrylamide and hydropropylacrylate monomers in oil containing surfactants and dispersions, etc. After the polymerization is completed, the dispersion or emulsion is distilled to remove water providing a dewatered dispersion or emulsions of polymer soil adsorbing particles with residual water less than 5%. The resulting oil-based polymer dispersion or emulsion can then be used as a polymer soil adsorbing agent of the present invention by applying it to a surface of a fibrous structure and/or multi-ply fibrous structure, such as a paper towel or two-ply paper towel, such as via spraying, slot extruding, printing, and/or other suitable known application methods. The fibrous structure plies and/or two-ply paper towel product may be embossed prior to and/or subsequent to the application of the polymer soil adsorbing agent.

Example 8

A hydroxypropylacrylate-polyacrylamide copolymer in powder form is prepared by spray drying the aqueous polymer solution from Example 5 above. Alternatively, it can be prepared by organic solvent extraction process of the oil-based dispersion or emulsion from Example 6 or 7 above. The resulting dry polymer soil adsorbing powders can be used as a polymer soil adsorbing agent of the present invention by applying it to a surface of a fibrous structure and/or multi-ply fibrous structure, such as a paper towel or two-ply paper towel, such as via powder-spraying. The fibrous structure plies and/or two-ply paper towel product may be embossed prior to and/or subsequent to the application of the polymer soil adsorbing agent.

Example 9

A hydroxypropylacrylate-polyacrylamide copolymer in inverted hydrogel form is prepared by adding water into the oil-based dispersion or emulsion from Example 6 or 7. The resulting fluid contains the copolymer in hydrogel form together with other fluid ingredients including oil, water, and surfactants. The copolymer inverted hydrogel can be used as a polymer soil adsorbing agent of the present invention by applying it to a surface of a fibrous structure and/or multi-ply fibrous structure, such as a paper towel or two-ply paper towel, such as via slot coating, brushing, printing, and/or other suitable application methods. The fibrous structure plies and/or two-ply paper towel product may be embossed prior to and/or subsequent to the application of the polymer soil adsorbing agent.

Example 10

A hydroxypropylacrylate-polyacrylamide copolymer in hydrogel form is prepared by conventional free-radical solution polymerization. By adjusting process parameter including but not limited to % solids, water levels, and/or addition of rheology modifiers, the bulk viscosity and final form of the polymer can be controlled to form the hydrogel. The copolymer hydrogel can be used as a polymer soil adsorbing agent of the present invention by applying it to a surface of a fibrous structure and/or multi-ply fibrous structure, such as a paper towel or two-ply paper towel, such as via slot coating, brushing, printing, and/or other suitable application methods. The fibrous structure plies and/or two-ply paper towel product may be embossed prior to and/or subsequent to the application of the polymer soil adsorbing agent.

Test Methods

Unless otherwise specified, all tests described herein including those described under the Definitions section and the following test methods are conducted on samples that have been conditioned in a conditioned room at a temperature of 23° C.±1.0° C. and a relative humidity of 50%±2% for a minimum of 2 hours prior to the test. All plastic and paper board packaging articles of manufacture must be carefully removed from the paper samples prior to testing. The samples tested are "usable units." "Usable units" as used herein means sheets, flats from roll stock, pre-converted flats, and/or single or multi-ply products. Except where noted all tests are conducted under the same environmental conditions and in such conditioned room. Any damaged product is discarded. Test samples with defects such as wrinkles, tears, holes, and like are not tested. Samples conditioned as described herein are considered dry samples (such as "dry filaments") for testing purposes. All instruments are calibrated according to manufacturer's specifications.

Accelerated and Stress Aging Procedures

Finished Product stability is defined as the ability of the Finished Product to deliver its intended performance after subjection to the normal range of storage, delivery, and retail conditions. Finished product rolls were packaged using 0.6 mil low density polyethylene film (a proprietary film, Extrel EX1560 available from Tredegar Corporation for this limited purpose) following the procedure detailed below:

1. Cut a 2×3 ft section of 0.6 mil low density polyethylene film.

2. Lay two finished product rolls of paper towels on poly film about 4 inches from the edge of the film such that the rolls are aligned with the 3 ft dimension, and fold poly along the length of the poly over top of the length of the rolls.
3. Heat seal the fold using 3 parallel seals ⅓ inch between each parallel line to insure an effective seal along the length of the rolls.
4. Heat seal on one end about an inch from the end of the poly. This forms a "sock" around the two rolls.
5. Taking care to minimize the volume of air that remains within the finished package, heat seal the final end an inch from the final edge of the 3 ft length of poly forming an airtight seal around the rolls.

The relatively long tail on the package permits samples to be taken off the rolls for testing, resealed and returned to a conditioned room described below for additional aging. Accelerated and Stress aging conditions are as follows:

Accelerated Aging (40° C.±2°, 75% RH±5% for 3 months);

Stress Aging (50° C.±2°, 60% RH±5% for 2 weeks, optionally extended to 3 weeks);

Samples are taken for testing by removing the package from the conditioned room, cutting the end of the package near as possible to the heat seal, remove the rolls, remove 2 sheets from the outside of the rolls and discard, remove 4 full size sheets for mirror cleaning testing and 1 additional sheet for soil retention. Place rolls back into package, and heat seal the top where it was cut and place back into the conditioned room for additional aging if necessary. Product aging without packaging under ambient lab conditions (23° C.±1.0° C. and a relative humidity of 50%±2%) has been shown to not occur, therefore test sheets removed from the high conditioned room can be stored under ambient lab conditions without undergoing additional aging before testing.

UL Viscosity Test Method
1) Reagents and Equipment
   a) NaCl,
   b) Deionized water,
   c) 9 moles Ethoxylated Nonyl Phenol (for example SYNPERONIC NP9 from ICI surfactant),
   d) Mechanical stirrer fitted with a stainless steel shaft equipped at the end with about 2 cm radius propeller-type blades,
   e) High tall 600 ml beaker,
   f) Disposable syringes (5 ml, 2 ml and 10 ml)
   g) Balance with an accuracy of 0.001 g,
   h) Thermometer,
   i) 200 μm stainless steel screen.
2) Preparation of an initial 0.5% polymer solution in water
   a) Obtain a clean 600 ml beaker and fill it with 100 g of deionized water,
   b) Start stirring with the mechanical stirrer at 500 rpm to create a vortex,
   c) Calculate the weight of pure emulsion ($W_0$) required to obtain 0.5 g of polymer, $W_0 = 50/C$ C is the percentage of active matter in the dispersion or emulsion
   d) Withdraw approximately the weight ($W_0$) of emulsion into a plastic syringe,
   e) Weigh accurately the syringe and record the weight filled ($W_F$),
   f) Disperse rapidly the contents of the syringe into the vortex of the beaker,
   g) Let stir 30 minutes,
   h) Weigh the empty syringe and record the weight empty ($W_E$),
   i) Calculate $W = W_F - W_E$.
3) Preparation of a 0.1% solution of polymer in 1 M NaCl
   a) Remove the beaker from the stirrer let the shaft and the blade, drain completely over the beaker,
   b) Place the beaker on the balance and weigh in accurately:
      i) 0.2 g of ethoxylated nonyl phenol
      ii) ($Q_E$) g of deionized water, where $Q_E = W \times (9.7949 \times C - 1) - 100.2$,
   c) Let it stir again for 5 minutes at 500 rpm,
   d) Then add the salt $Q_S$ in g: let it stir for 5 minutes, where $Q_S = 0.585 \times W \times C$,
   e) Resulting in a 0.1% solution of polymer in 1 M NaCl,
   f) The polymer solution is now ready for measurement after filtration through a 200 μm screen.
4) In the Case of a High Molecular Weight Emulsion (UL Viscosity greater than 7 cP)
   a) Prepare the solution at 0.5% as in step 2.
   b) Remove the beaker from the stirrer let the shaft and the blade drain completely over the beaker,
   c) Place the beaker on the balance and weight accurately:
      i) 0.2 g of ethoxylated nonyl phenol,
      ii) ($Q_E$) g of deionized water where $Q_E = W \times (9.7949 \times C - 1) - 100.2$,
   d) Let it stir again for 5 minutes at 850 rpm,
   e) Then add the salt $Q_S$ in g; let it stir for 5 minutes at 850 rpm, where $Q_S = 0.585 \times W \times C$
   f) Resulting in a 0.1% solution of polymer in 1 M NaCl,
   g) The polymer solution is now ready for viscosity measurement after filtration through a 200 μm screen.
5) Viscosity Measurement of Polymer Solution
   The viscosity is determined by means of a Brookfield viscometer model LVT with the UL adapter and a spindle speed of 60 rpm
   a) 16 ml of the solution are placed in the cup, and the temperature is adjusted to 23-25° C. the cup is then attached to the viscometer.
   b) Let the spindle turn at 60 rpm until the reading is stable on the dial (about 30 seconds);
   c) Read the value indicated on the dial:

Viscosity (in cP) = (reading −0.4)×0.1

Basis Weight Test Method

Basis weight of a fibrous structure, such as sanitary tissue product, is measured on stacks of twelve usable units using a top loading analytical balance with a resolution of ±0.001 g. The balance is protected from air drafts and other disturbances using a draft shield. A precision cutting die, measuring 3.500 in ±0.0035 in by 3.500 in ±0.0035 in is used to prepare all samples.

With a precision cutting die, cut the samples into squares. Combine the cut squares to form a stack twelve samples thick. Measure the mass of the sample stack and record the result to the nearest 0.001 g.

The Basis Weight is calculated in lbs/3000 ft$^2$ or g/m$^2$ as follows:

Basis Weigh=(Mass of stack)/[(Area of 1 square in stack)×(No. of squares in stack)]

For example,

Basis Weight (lbs/3000 ft$^2$)=[[Mass of stack (g)/ 453.6 (g/lbs)]/[12.25 (in$^2$)/144 (in$^2$/ft$^2$)×12]]× 3000 or,

Basis Weight (g/m$^2$)=Mass of stack (g)/[79.032 (cm$^2$)/10,000 (cm$^2$/m$^2$)×12]

Report result to the nearest 0.1 lbs/3000 ft$^2$ or 0.1 g/m$^2$. Sample dimensions can be changed or varied using a similar precision cutter as mentioned above, so as at least 100 square inches of sample area in stack.

Molecular Weight Test Method

The weight average molecular weight (Mw) of a material, such as a polymer, is determined by Gel Permeation Chromatography (GPC) using a mixed bed column. A high performance liquid chromatograph (HPLC) having the following components: Millenium®, Model 600E pump, system controller and controller software Version 3.2, Model 717 Plus autosampler and CHM-009246 column heater, all manufactured by Waters Corporation of Milford, Mass., USA, is utilized. The column is a PL gel 20 μm Mixed A column (gel molecular weight ranges from 1,000 g/mol to 40,000,000 g/mol) having a length of 600 mm and an internal diameter of 7.5 mm and the guard column is a PL gel 20 μm, 50 mm length, 7.5 mm ID. The column temperature is 55° C. and the injection volume is 200 μL. The detector is a DAWN® Enhanced Optical System (EOS) including Astra® software, Version 4.73.04 detector software, manufactured by Wyatt Technology of Santa Barbara, Calif., USA, laser-light scattering detector with K5 cell and 690 nm laser. Gain on odd numbered detectors set at 101. Gain on even numbered detectors set to 20.9. Wyatt Technology's Optilab® differential refractometer set at 50° C. Gain set at 10. The mobile phase is HPLC grade dimethylsulfoxide with 0.1% w/v LiBr and the mobile phase flow rate is 1 mL/min, isocratic. The run time is 30 minutes.

A sample is prepared by dissolving the material in the mobile phase at nominally 3 mg of material/1 mL of mobile phase. The sample is capped and then stirred for about 5 minutes using a magnetic stirrer. The sample is then placed in an 85° C. convection oven for 60 minutes. The sample is then allowed to cool undisturbed to room temperature. The sample is then filtered through a 5 μm Nylon membrane, type Spartan-25, manufactured by Schleicher & Schuell, of Keene, N.H., USA, into a 5 milliliter (mL) autosampler vial using a 5 mL syringe.

For each series of samples measured (3 or more samples of a material), a blank sample of solvent is injected onto the column. Then a check sample is prepared in a manner similar to that related to the samples described above. The check sample comprises 2 mg/mL of pullulan (Polymer Laboratories) having a weight average molecular weight of 47,300 g/mol. The check sample is analyzed prior to analyzing each set of samples. Tests on the blank sample, check sample, and material test samples are run in duplicate. The final run is a run of the blank sample. The light scattering detector and differential refractometer is run in accordance with the "Dawn EOS Light Scattering Instrument Hardware Manual" and "Optilab® DSP Interferometric Refractometer Hardware Manual," both manufactured by Wyatt Technology Corp., of Santa Barbara, Calif., USA, and both incorporated herein by reference.

The weight average molecular weight of the sample is calculated using the detector software. A dn/dc (differential change of refractive index with concentration) value of 0.066 is used. The baselines for laser light detectors and the refractive index detector are corrected to remove the contributions from the detector dark current and solvent scattering. If a laser light detector signal is saturated or shows excessive noise, it is not used in the calculation of the molecular mass. The regions for the molecular weight characterization are selected such that both the signals for the 90° detector for the laser-light scattering and refractive index are greater than 3 times their respective baseline noise levels. Typically the high molecular weight side of the chromatogram is limited by the refractive index signal and the low molecular weight side is limited by the laser light signal.

The weight average molecular weight can be calculated using a "first order Zimm plot" as defined in the detector software. If the weight average molecular weight of the sample is greater than 1,000,000 g/mol, both the first and second order Zimm plots are calculated, and the result with the least error from a regression fit is used to calculate the molecular mass. The reported weight average molecular weight is the average of the two runs of the material test sample.

For measuring the absolute molecular weight of aqueous polymers, Multiple Angle Laser-Light Scattering (MALS) is used.

Equipment

Waters Alliance 2695 Separations Module Wyatt Rex interferometric refractometer Wyatt Heleos II 18 angle laser light scattering detector Column Set 0.1M Aqueous Sodium Acetate to Acetonitrile 3:1
UHG1000 WAT011535 SN 4PNM100561
UHG500 WAT011530 SN PNM100531
UHG250 WAT011525 SN 02PN100911

Settings

Flow rate: 0.5 mL/min at RT
Injection volume: 100 μl
Run time: 70 mindn/dc: 0.14 for PAM Wyatt Heleos II Installation The Wyatt Heleos II is a multi-angle laser-light scattering (MALS) detector that measures absolute molecular weight of polymer eluting from a conventional GPC column set. There is no need for a polystyrene vs retention time calibration curve to arrive at the molecular weight distribution. The eluent from a GPC column is plumbed first into the Helios detector then into a concentration (RI) detector. The Helios contains a flow cell where laser-light scattering is measured over 18 angles. Wyatt's ASTRA software collects the data and generates a report containing the molecular weight information. The following steps are performed by Wyatt Technology after purchase:

Install the Helios into the GPC plumbing chain.
Install ASTRA software.
Make appropriate connections from instruments, computer and Waters 2695.
Calibrate detector 11 (90°) using filtered anhydrous toluene.
Calibrate all other detectors to detector 11 using an isotropic scatterer in the chosen solvent. This process is called normalization.
Determine the interdetector delay.
Verify the entire installation is performing satisfactorily by running a higher molecular weight standard in the chosen solvent with a known dn/dc.

Sample Execution

Samples for GPC MALS are prepared at ~2.0 mg/mL in eluent, filtered using 0.45μ nylon filters into autosampler vials and loaded into the carousel of the Waters 2695.

In ASTRA a new blank sequence is requested from the file menu.

In the sequence configuration pane a comment can be recorded, the ASTRA method is specified and the number of samples is recorded.

In the sequence sample table pane a row of information about each sample is entered. This is commonly just the sample name, do/dc and concentration. The duration of the run is specified by the method.

The sequence is started. The sequence is verified and ASTRA waits for an auto injection signal form the Waters 2695.

The samples in the Waters 2695 HPLC are started. The auto injection signal from the Waters 2695 causes ASTRA to begin collecting data from the detectors. The signal is visible in the Sequence sample graph pane as the samples runs.

Completion of the run causes ASTRA to save the data with the specified name and wait for the next sample or end the run as appropriate.

DATA Analysis

An experiment is opened in ASTRA for workup. At this point the experiment contains only the raw data. Pressing the reprocess button on the toolbar will invoke ASTRA to finish processing the data.

ASTRA will prompt you to draw a baseline for detector 11.

Pressing the set all button will construct similar baselines for the other angles as well as the RI detector.

Inspect other detector baselines; especially the RI detector and make changes as needed.

Click OK

ASTRA will prompt you to define the peak region.

Drag an area that contains the entire RI trace. For a polyoil this includes the area containing the leading edge of high molecular weight sample to the tailing edge of the peak where unmodified oil elutes. Low molecular weight olefins are excluded from polyoil molecular weight analysis.

Press OK.

ASTRA finished all calculations and prepares a summary report.

Moisture Content Test Method

The moisture content present in an article of manufacture, such as a fibrous structure is measured using the following Moisture Content Test Method. An article of manufacture or portion thereof ("sample") is placed in a conditioned room at a temperature of 23° C.±1.0° C. and a relative humidity of 50%±2% for at least 24 hours prior to testing. Each fibrous structure sample has an area of at least 4 square inches, but small enough in size to fit appropriately on the balance weighing plate. Under the temperature and humidity conditions mentioned above, using a balance with at least four decimal places, the weight of the sample is recorded every five minutes until a change of less than 0.5% of previous weight is detected during a 10 minute period. The final weight is recorded as the "equilibrium weight". Within 10 minutes, the sample is placed into a forced air oven on top of foil for 24 hours at 70° C.±2° C. at a relative humidity of 4%±2% for drying. After the 24 hours of drying, the sample is removed and weighed within 15 seconds. This weight is designated as the "dry weight" of the sample.

The moisture content of the sample is calculated as follows:

$$\% \text{ Moisture in sample} = 100\% \times \frac{(\text{Equilibrium weight of sample} - \text{Dry weight of sample})}{\text{Dry weight of sample}}$$

The % Moisture in sample for 3 replicates is averaged to give the reported % Moisture in sample. Report results to the nearest 0.1%.

Soil Adsorption Test Method

In order to measure an article of manufacture's Average Soil Adsorption Value the following test is conducted.

Preparation:

A specimen of the article of manufacture, such as a fibrous structure, to be tested is obtained from the central portion of a representative sample of the article of manufacture. The specimen is prepared by cutting a CD strip (extending across the entire CD of the article of manufacture) from an article of manufacture, such as a finished fibrous structure and/or sanitary tissue product sheet (sample) such that the cut CD strip specimen has a length and width resulting in the specimen weighing 0.65 g±0.02 g. The sheet of the sample from which the CD strip specimen is cut may be delineated and connected to adjacent sheets by perforation or tear lines or the sheets of the sample may be individual sheets, such as in the form of individual wipes and/or facial tissues. If connected via perforation or tear lines, then separate one sheet from any adjacent sheet before cutting the CD strip from the sheet. The CD strip specimen needs to be free of perforations and is obtained from a portion of an article of manufacture at least 0.5 inches from any perforations. The specimen is conditioned as described above. The sample weight ($W_{Prod}$) is recorded to the within ±0.0001 g. A suitable ball-point pen or equivalent marker is used to write the specimen name onto a corner of the specimen.

A centrifuge tube (VWR brand 50 mL superclear ultra high performance freestanding centrifuge tube with flat caps, VWR Catalog #82018-052; or equivalent tube) is labeled with the specimen name and weighed to within ±0.1 mg $W_{CT}$. Next, 155.0 mg±5.0 mg of a model soil (black todd clay) available from Empirical Manufacturing Co., 7616 Reinhold Drive, Cincinnati, Ohio 45237-3208, is placed into the centrifuge tube. The tube is re-weighed $W_{(CT+Soil)}$ and the model soil weight ($W_{Soil}$) is determined to nearest 0.2 mg by difference $W_{(CT+Soil)} - W_{CT}$.

Distilled water, 35 g±0.5 g is added slowly to the centrifuge tube using a suitable dispenser. The centrifuge tube is a VWR brand 50 mL superclear ultra high performance freestanding centrifuge tube with flat caps (VWR Catalog #82018-052, or equivalent tube). The distilled water is poured carefully into the centrifuge tube to avoid causing a plume of dust from the model soil. If a plume of dust occurs such that the weight of soil in the tube may be impacted, the tube is discarded and a new tube is prepared. The tube is then re-weighed $W_{(CT+Soil+Water)}$ and the total weight ($W_{(Soil\ Dispersion)}$) of water plus soil in the centrifuge tube is calculated by subtracting the weight of the centrifuge tube $W_{CT}$ from the $W_{(CT+Soil+Water)}$ and recorded to the nearest 0.2 mg.

A glass petri dish (e.g. VWR 50×35, VWR Catalog #89000-280, or equivalent dish) is labeled and weighed to within 0.1 mg ($W_{(Petri\ Dish)}$).

Testing:

A reciprocating shaker is used to disperse the model soil in the water. The model soil must be completely dispersed for the results to be valid. A reciprocating shaker (IKA Works HS 501 digital reciprocating shaker, number 2527001, with a Universal attachment, number 8000200, or equivalent shaker) is set to 300±3 cycles per minute. The capped centrifuge tube containing the model soil and water is mounted in the shaker and shaken for 30 seconds to obtain a uniform dispersion of the soil in the water (soil dispersion).

The specimen is loosely folded along its transverse centerline with an accordion style (paper fan) folding technique. The specimen is loosely folded 5 times, to produce a sample that contains 10 segments each about 2.5 cm in length. This folding technique keeps the sample from being too tightly folded, which may hinder free flow of water and suspended soil over all surfaces of the article the thus efficiency of the paper to adsorb the soil. The folded sample is fully immersed into the soil dispersion in the centrifuge tube so that the folds run parallel to the length of the centrifuge tube. The tube is immediately re-capped and shaken in the reciprocating shaker for 30±1 seconds with the length axis of the centrifuge tube parallel to the motion of the reciprocating shaker.

Immediately after shaking, the folded specimen is carefully removed over the glass petri dish using laboratory tweezers. Care must be taken to ensure that greater than 95% of the soil dispersion is kept either in the original centrifuge tube or corresponding glass petri dish. The soil dispersion is wrung (removed) from the specimen using a "wringing" motion and collected in the glass petri dish. Once the soil dispersion has been removed from the specimen, the specimen is discarded. The remaining soil dispersion is poured from the centrifuge tube into the glass petri dish after swirling the mixture to re-disperse model soil into water, thereby ensuring that no model soil is inadvertently left behind in the centrifuge tube. The glass petri dish containing the model soil/water mixture is weighed to within ±0.1 mg $W_{(Petri\ Dish+Soil\ Dispersion)}$. The weight of soil dispersion recovered $W_{(Recovered\ Soil\ Dispersion)}$ is calculated by subtracting the weight of the glass petri dish $W_{(Petri\ Dish)}$ from the $W_{(Petri\ Dish+Soil\ Dispersion)}$. The glass petri dish is then placed into a vented laboratory drying oven at 105° C. until the sample of residual soil is fully dry. The $W_{(Recovered\ Soil\ Dispersion)}$ should be >95% of the $W_{(Soil\ Dispersion)}$.

Once the sample is dry, the glass petri dish containing the dried model soil is removed from the oven and placed in a desiccator until cool and then re-weighed to within ±0.1 mg $W_{(Petri\ Dish+Residual\ Dry\ Soil)}$. The weight of residual soil $W_{(Residual\ Soil)}$ is calculated by subtracting the weight of the glass petri dish $W_{(Petri\ Dish)}$ from $W_{(petri\ Dish+Residual\ Dry\ soil)}$ and recorded to the nearest 0.2 mg.

Calculations:

To calculate the amount of residual model soil $W_{(Residual\ Residual\ Soil)}$ left in the glass petri dish, the following equation is used:

$$W_{(Residual\ Soil)} = W_{(Petri\ Dish+Residual\ Dry\ Soil)} - W_{(Petri\ Dish)}$$

Residual model soil weight ($W_{(Residual\ Soil)}$) is reported in mg.

To calculate the amount of normalized residual model soil ($W_{(Norm\ Residual\ Soil)}$) left in the glass petri dish, the following equation is used:

$$W_{(Norm\ Residual\ Soil)} = W_{(Residual\ Soil)} * W_{(Soil\ Dispersion)} / W_{(Recovered\ Soil\ Dispersion)}$$

Normalized residual soil weight $W_{(Norm\ Residual\ Soil)}$ is reported in mg.

To calculate the amount of soil adsorbed by the sample, the following calculation is used:

$$W_{(Soil\ Adsorbed)} = (W_{(Soil)} - W_{(Norm\ Residual\ Soil)}) / W_{(Prod)}$$

Soil adsorbed in sample $W_{(Soil\ Adsorbed)}$ is reported as mg soil/g article of manufacture.

The test is performed on three replicates and an Average Soil Adsorption Value (Avg $W_{(Soil\ Adsorbed)}$) is calculated for the article of manufacture. These values are measured and calculated for initial Average Soil Adsorption Value of a specimen prior to subjecting the specimen to the Accelerated and Stress Aging Procedures described herein and after subjecting the specimen to the Accelerated and Stress Aging Procedures described herein. Soil Adsorption Value is also referred to herein as mg Soil Retained/gram Paper and its corresponding % Soil Retained (by Paper).

Mirror Cleaning Test Method

A test stand cart holding 4 individual 28"×28" mirrors (one on each of the 4 sides) resting on a flat surface, such as a floor, is utilized for the mirror cleaning test. The silver mirror layer is on the back surface of a flat clear glass sheet approximately 5 mm thick. The cart is configured such that the bottom edge of each mirror is approximately 3'6" off the flat surface.

The mirror is prepared for testing by cleaning as follows: 1) Windex® commercially available from SC Johnson (an alkaline composition (pH>9) containing 0.1-1.0% by weight of Ethyleneglycol Monohexylether, 1.0-5.0% by weight of Isopropanol, 0.1% sodium lauryl sulfate, 0.05-28% ammonia, and 90-100% by weight of Water) or equivalent is sprayed (4 full sprays, about 3.5 g of solution) onto the mirror surface which is then spread across the entire surface of the mirror with 2 sheets of a 1-ply paper towel, for example 2010 commercially available Bounty® Basic (folded into quarters) using a circular wiping motion; 2) the mirror surface is then wiped dry and lightly polished with the essentially dry side of the folded 1-ply paper towel; 3) wiping the mirror surface with an additional two sheets of the 1-ply paper towel saturated with deionized water; and 4) using a squeegee in a top to bottom motion to remove all excess deionized water. Steps 3) & 4) may be repeated as necessary to achieve a streak and smudge free mirror surface that has no residual impact on the cleaning performance of subsequent test articles of manufacture. Any suitable absorbent substrate can be used in place of Bounty Basic that is not impregnated with polymers that may be deposited onto the glass surface, which may impact the ease or difficulty of cleaning with subsequent test article of manufacture.

A model soil suspension is prepared by suspending 1% by weight of Black Todd Clay in a 50/50 weight ratio of water/isopropyl alcohol mixture containing 0.05% by weight of 100% soybean oil (viscosity of from 150 cP to 200 cP).

Preparation of 100% cooked soybean oil is as follows. Approximately 200 grams of 100% soybean oil available from Spectrum Chemical Manufacturing Corp., 14422 S. San Pedro St., Gardena, Calif. 90248 is placed in a 1000 mL beaker with stir bar. The soybean oil in the beaker is placed on a hot plate and heated to 204° C. while stirring slowly. Air is added through a glass pipette tip set to bubble continuously through the oil without splashing. The oil is cooked continuously until viscosity, at 25° C.±2.2° C., is between 150 and 200 cP. The color changes to a dark orange. Viscosity is measured using a Cannon-Ubbelohde Viscometer tube #350 available from Cannon Instrument Company, State College, Pa. 16803, or equivalent viscometer. A sample of oil which is near room temperature is added to the viscometer and equilibrated to 25° C. in a constant temperature water bath. The efflux time for the meniscus to pass from the top mark to the bottom mark is measured to within ±0.01 second while allowing the oil to flow through the viscometer tube under gravity. Kinematic viscosity in mm²/s is calculated by multiplying the time in seconds by the calibration constant supplied with the viscometer tube. Separately the fluid density is determined by measuring the weight of a fixed volume of oil using a 25 mL volumetric flask and a 4 place analytical balance. Viscosity in cP can be calculated by multiplying the Kinematic viscosity by density of oil in g/mL. The cooking time will vary depending on quantity, surface area and air flow through the oil.

The following procedure is used to apply model soil to the clean mirror surfaces. The target amount of model soil sprayed is 44 g±2.5 g. A spray bottle, part #0245-01 available from www.SKS-bottle.com or equivalent spray bottle is used to spray the model soil suspension onto the mirror surface. Fill the spray bottle to within about 0.5 to 1 inch of the top with the model soil suspension and weigh to the nearest 0.01 g and record as initial weight. The spray bottle is then manually pressurized as needed to achieve a dispersed spray of fine droplets (about 30 full pumps is recommended). Additional pressurization is required between each mirror (about 10 pumps is recommended). Holding the spray bottle about 1.5 feet from the mirror surface a substantially horizontal sweeping motion is used starting at the top of the mirror surface and working down to the bottom of the mirror surface traversing the mirror surface a total of 8 times while attempting to have relatively even coverage on the mirror surface. After applying the model soil suspension to all 4 mirrors, the spray bottle and remaining contents are weighed to the nearest 0.01 g and recorded as weight after first spray. The mirrors are dried sequentially using a hand-held hair dryer. The difference between the initial weight and after first spray is used to adjust the amount of spray applied in a second application to achieve the target amount of 44 g±2.5 g. If the amount of spray is too little or too much, discard the test sample and begin the test again. The second application of the model soil suspension is applied to each mirror surface in a circular motion, moving from the outside (approximately 8-10 inches from the side edges) inward toward the center. After drying the second application of model soil suspension the mirrors are ready to be cleaned with an article of manufacture ("specimen") to be tested. If the time between soil application and cleaning of the mirrors with a test sample extends past 30 minutes, the mirrors need to be returned to their pristine condition using the procedure defined previously after which the soil application procedure can be repeated.

A specimen of a test article of manufacture, for example a paper towel, is prepared as follows. Two sheets of the article of manufacture, for example a paper towel, may be delineated and connected to adjacent sheets by perforation or tear lines or the sheets of the sample may be individual sheets, such as in the form of individual wipes, napkins, and/or facial tissues. If the article of manufacture, for example a paper towel, is a select-a-size format, then 4 sheets are used. Individual sheet dimensions or in the case of select-a-size two sheets vary by brand from about 8.5"×11" to 14"×11" and 2.20 g to 5.2 g. The 2 or for select-a-size 4 sheet specimen is folded in half (along perforations if present) with the emboss side out (where applicable). The folded sample is then folded in half again with the crease perpendicular to the MD direction and then folded in half again perpendicular to the CD direction such that a sample pad of quarter size sheet that is 8 sheets thick is formed, each sheet may consist of 1, 2 or more individual plies. In the case of articles of manufacture with single side application of soil attracting polymer it is important to fold the sheet such that the side containing the soil attracting polymer directly contacts the surface of the mirror. The mirror surface is then treated with 5 full sprays of Windex: two at top; one in the center and two in the lower area of the mirror. The weight of Windex sprayed per mirror is about 4.35 g±0.36 g. The mirror surface is cleaned by grasping the sample pad in the hand, clamping the substrate between the thumb and index finger and wiping with firm pressure in a cross direction, while holding the sheet (side 1) as flat as possible upon the surface of the mirror and avoiding contacting the mirror with any part of the hand using 8 side-to-side passes, such that the full surface of the mirror is contacted. The sample pad is then turned over and the relatively dry back-side (side 2) is used to wipe the mirror surface in an up and down motion, with firm pressure applied using 14 passes, ensuring that the entire surface of the mirror is contacted, again holding the sample pad as flat against the mirror surface as possible. The sample pad is then unfolded once and then folded back on itself revealing a relatively fresh sample pad surfaces to clean the second mirror after application of Windex as discussed above; side 3 (opposite side 1) is used for the side-to-side wiping and then turned over to side 4 (opposite side 2) for the up and down wiping. The pad is then unfolded twice to reveal a fresh surface of the specimen. The specimen is then folded in half such that the fresh sample surface is visible with the two used areas of the first sample pad configuration (sides 1 and 3) facing each other and then folded again to clean the third mirror surface after application of Windex as discussed above. Side 5 opposite side 1 and 3 is used first and then turned over to side 6 for the second up and down wiping. The sample pad is unfolded once and then folded back on itself revealing sides 7 and 8 to clean the fourth mirror surface after application of Windex as discussed above. Side 7 opposite sides 5, 3 & 1 is used for the side-to-side wiping and then turned over to side 8 for the final up and down wiping. In each case the wettest part of the folded sample pad is used for the side-to-side wiping and the dryer side for the final up and down wiping.

All 4 mirror surfaces should be cleaned sequentially such that minimal drying of the specimen pad occurs. After cleaning all four mirror surfaces, the mirror surface is permitted to dry and each mirror surface's optical density is measured utilizing an X-Rite 518 Spectrodensitometer. A full calibration as described in the operator's manual is performed. The instrument is set-up per instructions in the manual in Density minus Reference Measurement Mode. The four 28"×28" mirror surfaces that were cleaned as described above representing a pristine condition. A single reading of a mirror in pristine condition is completed and stored as Ref1 and is used as a reference for all subsequent measurements. A series of 9, 12, or 15 measurements are made on each of the 4 mirrors (3, 4, or 5, respectively, across the top, 3, 4, or 5, respectively, across the middle and 3, 4, or 5, respectively, across the bottom always maintaining a minimum of 3 inches from any edge of the mirror). The mirror cleaning test stand is oriented in the lab such that there is no direct overhead lighting and rotated such that the mirror being measured is facing towards an interior wall thus minimizing any influence caused by external lighting differences. Measurements were performed on each of the pristine mirrors. These 9, 12, or 15 individual values are averaged for each mirror. The average values were found to be consistent between mirrors, however, as expected the average shows a small difference from the single point reference. This difference is used to correct all subsequent average values measured. Additionally, average values were determined for mirrors after application of the model soils. After, following the cleaning procedure with the sample specimen, 9, 12, or 15 density readings are performed and an average Densitometer Value is reported for each of the individual mirrors. The Average Mirror Cleaning Densitometer Value is the average of the average Densitometer Values across all 4 mirrors. The orientation of the mirrors and room lighting is such that streaks are not readily visible thus insuring a random location of each measurement taken within the limitations of the 3×3, 3×4, or 3×5 grid described above.

Volatile Organic Carbon (VOC) Test Method

The VOC content of an article of manufacture, expressed in units of weight of VOC per weight of polymer (soil adsorbing agent(s)), and shall be determined as follows. The VOC content of water in oil emulsions and dewatered emulsions is determined utilizing EPA method 24. Specifically the following procedure was utilized:

% volatiles:
1. Weigh a dry aluminum drying pan utilizing a 4 place analytical balance.
2. Equilibrate sample by gently mixing to insure representative sampling.
3. Add approximately 1 gram of neat material (sample) to the pre-weighed aluminum drying pan and weigh on the 4 place analytical balance.
4. Weight in step 3 minus the weight in step 1 equals the sample weight.
5. Place aluminum drying pan with sample into oven at 105° C. for 1 hour.
6. Remove the aluminum drying pan and dry sample from oven and place in a dessicator to cool.
7. Reweigh aluminum drying pan+dried and cooled sample on 4 place analytical balance.
8. Difference in weight of step 7 minus step 1 equals the residual weight.
9. Residual weight determined in step 8 divided by the sample weight in step 4×100=% solids at 105° C.
10. 100 minus % solids determined in step 9 equals % volatile at 105° C.

% moisture by Karl Fischer:

The industry standard volumetric titration using a Metler DL18 or DL31 Karl Fischer specific titrator, a two component reagent system and a Mettler DM143-SC double platinum pin electrode can be used. Alternatively, moisture can be determined by ASTM D 4017.

% VOC:

% VOC=% Volatiles−% Moisture.

Charge Density Test Method

If one has identified or knows the soil adsorbing agent in and/or on an article of manufacture, then the charge density of the soil adsorbing agent can be determined by using a Mutek PCD-04 Particle Charge Detector available from BTG, or equivalent instrument. The following guidelines provided by BTG are used. Clearly, manufacturers of articles of manufacture comprising soil adsorbing agents know what soil adsorbing agent(s) are being included in their articles of manufacture. Therefore, such manufacturers and/or suppliers of the soil adsorbing agents used in the articles of manufacture can determine the charge density of the soil adsorbing agent.

1. Start with a 0.1% solution (0.1 g soil adsorbing agent+99.9 g deionized water). Preparation of dilute aqueous solutions in deionized water from inverse or dewatered inverse dispersions or emulsions are performed as instructed by the supplier of the dispersion or emulsions and is well known to one of ordinary skill in the art. Depending on the titrant consumption increase or decrease the soil adsorbing agent content. Solution pH is adjusted prior to final dilution as charge density of many additives is dependent upon solution pH. A pH of 4.5 is used here for cationic polymers and between 6-7 for anionic polymers. No pH adjustment was necessary for the anionic polymers included in this study.
2. Place 20 mL of sample in the PCD measuring cell and insert piston.
3. Put the measuring cell with piston and sample in the PCD, the electrodes are facing the rear. Slide the cell along the guide until it touches the rear.
4. Pull piston upwards and turn it counter-clock-wise to lock the piston in place.
5. Switch on the motor. The streaming potential is shown on the touch panel. Wait 2 minutes until the signal is stable.
6. Use an oppositely charged titrant (for example for a cationic sample having a positive streaming potential: use an anionic titrant). Titrants are available from BTG consisting of 0.001N PVSK or 0.001N PolyDADMAC.
7. An automatic titrator available from BTG is utilized. After selecting the proper titrant, set the titrator to rinse the tubing by dispensing 10 mL insuring that all air bubbles have been purged.
8. Place tubing tip below the surface of the sample and start titration. The automatic titrator is set to stop automatically when the potential reaches 0 mV.
9. Record consumption of titrant, ideally, the consumption of titrant should be 0.2 mL to 10 mL; otherwise decrease or increase soil adsorbing agent content.
10. Repeat titration of a second 20 mL aliquot of the soil adsorbing agent sample.
11. Calculate charge demand (solution) or charge demand (solids);

$$\text{Charge demand}(eq/L) = \frac{V \text{ titrant used}(L) \times \text{Conc. of titrant in Normality}(eq/L)}{\text{Volume of sample titrated}(L)}$$

$$\text{Charge demand}(eq/g) = \frac{V \text{ titrant used}(L) \times \text{Conc. of titrant in Normality}(eq/L)}{Wt. \text{ solids of the sample or its active substance}(g)}$$

The charge density (charge demand) of a soil adsorbing agent is reported in meq/g units.

Acrylamide Monomer Test Method

Acrylamide is prepared for analysis from an article of manufacture by extracting 1 gram of the article with 20 mL of Analytical Reagent Grade Water (ARW). The analyte and internal standard ($^{13}C_3$-acrylamide) are subjected to reversed-phase high performance chromatographic (RP-HPLC) analysis on a Phenomenex Synergi Hydro-RP column (2.1×150 mm, 4 µm, 80 Å). Detection and quantification is by tandem mass spectrometry (MS/MS) operating under multiple reaction monitoring (MRM) conditions. Calibration standards (STD) prepared in ARW are used to quantitate Quality Control (QC) samples and unknown specimens. The nominal range of quantitation is 0.5 to 100 ng/mL. The assay requires a 0.2 mL aliquot of ARW extract of article. Specimen concentrations are determined by back-calculation using a weighted ($1/x^2$) quadratic calibration curve generated from neat STDs.

Reagents:
1. Acrylamide. Sigma-Aldrich,
2. $^{13}C_3$-Acrylamide. Isotec.
3. Methanol (MeOH). EMD, HPLC grade, cat #MX0475P-1; or equivalent.
4. Acetonitrile (ACN). EMD, HPLC grade, cat #AX0145; or equivalent.
5. Formic Acid. EMD, cat #11670; or equivalent.
6. Analytical Reagent Grade Water (ARW); or equivalent.
7. Needle Wash 1: ARW with 0.1% FA. Expires after 3 months stored at room temperature. (Example: Combine 1000 mL of ARW with 1 mL formic acid.)

8. Needle Wash 2: ACN with 0.1% FA. Expires after 6 months stored at room temperature. (Example: Combine 1000 mL of acetonitrile with 1 mL formic acid.)
9. Mobile Phase A: 4% MeOH/96% ARW (v/v) with 0.1% FA. Expires after 3 months stored at room temperature. (Example: Combine 960 mL of ARW and 40 mL of MeOH with 1 mL formic acid.)
10. Mobile Phase B: 95% MeOH/5% ARW (v/v) with 0.1% FA. Expires after 3 months stored at room temperature. (Example: Combine 950 mL of MeOH and 50 mL of ARW with 1 mL formic acid.)

Apparatus:
1. Electronic Dispensing Pipettes (EDP), manual pipettes; or equivalent.
2. HPLC pump. Shimadzu Model SCL-10A vp system controller & LC-10AD vp pumps with Gilson Model 811C mixer (65 µL volume); or equivalent.
3. Mass spectrometer. Sciex API 4000; or instrument meeting equivalent sensitivity requirements using analyst software.
4. Valco Two Position Actuator; or equivalent.
5. Analytical Column. Phenomenex Synergi Hydro-RP column (2.0×150 mm, 4 µm, 80 Å).
6. 20 mL Scintillation Vials, Wheaton, catalog #986541; or equivalent.
7. 50 mL polypropylene centrifuge tube.
8. Multi-Tube Vortexer. VWR brand; or equivalent.
9. Autosampler. CTC Analytics HTS PAL, Leap Technologies; or equivalent.
10. 1.3 mL Round Well Round Bottom Polypropylene 96-well Injection Plates. Microliter cat #07-3000, VWR cat #100532-120; or equivalent.
11. 1.3 mL Sealing Mat for Deep 96 Round Well Collection Plates. Axygen Scientific cat #AM-750UL-RD; or equivalent.

Procedure:
1. Preparation of Acrylamide Calibration Standards (STD) and Quality Control (QC) Samples
   Separate Stock solutions should be prepared for STD and QC samples to verify correctness of weighing. Standards and QC samples are prepared fresh daily.
   1.1. Acrylamide Standard Stock (STD Stock) and QC Stock (QC Stock) Solutions (1.00 mg/mL):
      Prepare separate two 1.00 mg/mL stocks of the compound, one for standards (STD Stock) and the other for QCs (QC Stock).
      Typical Preparation: Using the appropriate Analytical Reference Standard weigh approximately 5-20 mg into a Scintillation Vial and record the weight. Add calculated volume of water determined in Equation 1 to the vial. An ultrasonic cleaner may be used to assist dissolving the compound. Mix well and store at room temperature (about 23.0° C.). The stability is to be determined $$\text{Volume to add(ml)} = \frac{\text{Mass of material(mg)}}{1.00 \text{ mg/ml concentration}} \times \% \text{ Purity} \quad \text{Equation 1}$$

Where: Purity=Decimal % purity assigned to the Analytical Reference Standard multiplied by any salt correction factor.
   1.2. Standard (STD) Solutions and QC Solutions:
      With an adjustable volume pipette, add the appropriate amount of each Spiking Solutions, according to Table 2 below into an appropriate scintillation vials to make the indicated ng/mL STD or QC solutions. For makeup solution, dilute using water. Mix well and store at room temperature until use.

Preparation of Calibration Standard Curve and QC Samples.

TABLE 2

| Solution Used | Initial Conc (ng/mL) | Initial Volume (mL) | Solution Made | Final Conc (ng/mL) | Final Volume (mL) | Makeup |
|---|---|---|---|---|---|---|
| Stock | 1,000,000 | 0.10 | IMD | 10,000 | 10 | 9.90 |
| IMD | 10,000 | 0.10 | STD 9 | 100 | 10 | 9.90 |
| IMD | 10,000 | 0.08 | STD 8 | 80 | 10 | 9.92 |
| IMD | 10,000 | 0.04 | STD 7 | 40 | 10 | 9.96 |
| IMD | 10,000 | 0.02 | STD 6 | 20 | 10 | 9.98 |
| STD 9 | 100 | 1.00 | STD 5 | 10 | 10 | 9.00 |
| STD 7 | 40 | 1.00 | STD 4 | 4 | 10 | 9.00 |
| STD 6 | 20 | 1.00 | STD 3 | 2 | 10 | 9.00 |
| STD 5 | 10 | 1.00 | STD 2 | 1 | 10 | 9.00 |
| STD 4 | 4 | 1.25 | STD 1 | 0.5 | 10 | 8.75 |
| IMD | 10,000 | 0.075 | HQC | 75 | 10 | 9.925 |
| HQC | 75 | 2.0 | MQC | 15 | 10 | 8.00 |
| MQC | 15 | 1.0 | LQC | 1.5 | 10 | 9.00 |

2. Preparation of $^{13}C_3$-Acrylamide Internal Standard (ISTD) Solution.
   2.1. ~1.00 mg/mL Internal Standard Solution $^{13}C_3$-Acrylamide (ISTD Stock):
      Prepare a 1.00 mg/mL Stock Solution of compound.
      Typical Preparation: Weigh approximately 5 to 10 mg of compound in to Scintillation Vial and record the weight. Add calculated volume of water determined in Equation 1 to the vial. Mix well. An ultrasonic cleaner may be used to assist dissolving the compound. Store at 4° C. until use.
   2.2. ~10,000 ng/mL Internal Standard Intermediate Solution (ISTD IMD):
      Prepare a ~10,000 ng/mL Internal Standard Solution (W-ISTD) of $^{13}C_3$-Acrylamide by diluting 0.1 mL of the Stock Internal Standard Solution (2.1) with 9.9 mL of water. Mix well. Store at 4° C. until use.
   2.3. ~100 ng/mL Working Internal Standard Solution (W-ISTD):
      Prepare a ~100 ng/mL Working Internal Standard Solution (W-ISTD) of $^{13}C_3$-Acrylamide by diluting 0.1 mL of Internal Standard Intermediate Solution (2.2) with 9.9 mL of water. Mix well. Store at 4° C. until use.
4. Batch Preparation: A study batch includes bracketing calibration standards, quality control (QC) samples, blanks, and study specimens. At least one zero standard is placed after a high standard, high QC or suspected high study specimen.
   4.1. Original Samples and Matrix Blank: Weigh approximately 1 gram of an article of manufacture into a 50 mL polypropylene centrifuge tube and 20 mL of water is added. Vortex for approximately 10 minutes. For paper towel, weigh 1 sheet of paper towel into a suitable container and 100 mL of water is added. Vortex for approximately 10 minutes. For polymer solution, weigh approximately 10 mg of polymer solution and dilute it with water to an appropriate concentration.
   4.2. Working Internal Standard: Add 0.050 mL of the Working Internal Standard solution (W-ISTD as prepared in Section 2.2) into each well of a 96-well plate except for the Reagent Blank.
   4.3. Reagent Blank: Add 0.250 mL of water to all designated wells for reagent blanks and STD 0.

4.4. STD Samples. Add 0.200 mL of each calibration standard solution (STD 1-STD 9 prepared in Section 1.2) to its designated wells.

4.5. QC Samples. Add 0.200 mL of each quality control calibration solution (LQC, MQC and HQC prepared in Section 1.2) to its designated wells.

4.6. Samples. Add 0.200 mL of each sample to its designated wells.

4.7. Cover the plate with sealing mat and vortex the plate for approximately 10 seconds.

4.8. Analyze the samples by HPLC-MS/MS.

Analysis by HPLC-MS/MS

Using the instrument parameters listed below in Tables 3-5:

TABLE 3

HPLC-MS/MS Parameters
API 4000 Sciex MS with Shimadzu Pump and Leap Injector

| Flow rate | 0.30 mL/min |
|---|---|
| Injection volume | 10 μL* |
| Total Run time | 5 min |
| HPLC Column Temperature | Ambient |
| Pre Clean with Wash 1 | 2 |
| Pre Clean with Wash 2 | 0 |
| Post Clean with Wash 1 | 1 |
| Post Clean with Wash 2 | 1 |
| Valve Clean with Wash 1 | 1 |
| Valve Clean with Wash 2 | 1 |

*The injection volume may be adjusted to optimize the HPLC-MS/MS sensitivity.

TABLE 4

Gradient

| Time | Mobile Phase A (%) | Mobile Phase B (%) |
|---|---|---|
| 0.0 | 100 | 0 |
| 2.4 | 100 | 0 |
| 2.7 | 0 | 100 |
| 3.5 | 0 | 100 |
| 3.6 | 100 | 0 |
| 5.0 | 100 | 0 |

TABLE 5

| Time | Divert Valve |
|---|---|
| 0.0 | To Waste |
| 0.5 | To MS |
| 4.5 | To Waste |

Mass Spectrometer Parameters. These are typical operating conditions for the Sciex API 4000 mass spectrometer as shown in Table 6 below. These parameters may be adjusted to optimize the response; however, these parameters must not be adjusted during a run, but rather a consistent set of instrument settings/parameters must be used for each run.

TABLE 6

| Mass Spectrometer: | Sciex API 4000 |
|---|---|
| Ionization mode: | Turbo-Ion Spray-ESI |
| Polarity: | Positive |
| Turbo Temp: | 650° C. |
| CUR: | 30 |
| GS 1: | 75 |
| GS 2: | 75 |
| IS: | 3800 |
| CAD: | 12 |

TABLE 6-continued

| EP: | 10 |
|---|---|
| CXP: | 10 |
| Dwell: | 80 |

TABLE 7

Ions used in MRM mode

| Compound | Precursor Ion (m/z) | Product Ion (m/z) | DP | CE |
|---|---|---|---|---|
| Acrylamide | 71.9 | 55.1 | 36 | 17 |
| $^{13}C_3$-Acrylamide | 74.9 | 58.1 | 41 | 17 |

The molecular ions listed in Table 7 above may vary by ±0.2 m/z depending upon instrument calibration and optimization.

Regression Analysis:

A weighted ($1/x^2$) quadratic regression analysis is performed in Analyst for the observed signal (defined here as the peak area ratio of the analyte to its internal standard) as a function of the analyte mass.

System Suitability Criteria:

Visual inspection will ensure no significant peaks (<20% of the response of the lowest standard) at the retention time of the analyte.

That adequate retention and peak shape is obtained for the analyte and that following the high standard there is not significant carry over in a STD 0 (<20% of the response for lowest standard) for each analyte.

Standard Curve Acceptance Criteria:

The curve contains at least 5 unique non-zero standards and at least 75% of the standards analyzed must meet the accuracy (% RE) criteria.

% RE of each back calculated standard mass is ±15% (±20% for low standard)

QC Acceptance Criteria:

At least 67% of the total number of QC's run, and at least 50% of the QC's at each mass level (LQC, MQC & HQC), must meet the following accuracy acceptance criteria.

The % RE must be less than or equal ±15% at each QC level.

Bulk Viscosity Test Method

The purpose of this bulk viscosity test is to measure the viscosity of emulsions, such as dewatered emulsions, themselves.

Equipment:

Brookfield viscometer model LUT (or LVF) or equivalent;

Constant temperature bath at 25° C.;

250 mL capped bottles

Thermometer

Procedure:

Place 250 mL of the neat emulsion in a clean, dry bottle and close with cap.

Place bottle in a constant temperature bath set at 25° C. and allow the sample to equilibrate at 25° C. Immediately thoroughly mix the sample and then immediately, while sample is at 25° C., test the sample.

Measure the viscosity with the Brookfield viscometer using the suitable spindle at 30 rpm as set forth below in Table 8.

Let the spindle turn until the index is providing a stable reading (about 30 seconds).

TABLE 8

| Viscosity (in cps) = value × appropriate factor | | | |
|---|---|---|---|
| Spindle speed | LV1 | LV2 | LV3 |
| 30 rpm | ×2 | ×10 | ×40 |

CRT Test Method

The absorption (wicking) of water by an absorbent fibrous structure (sample) is measured over time. A sample is placed horizontally in the instrument and is supported by an open weave net structure that rests on a balance. The test is initiated when a tube connected to a water reservoir is raised and the meniscus makes contact with the center of the sample from beneath, at a small negative pressure. Absorption is allowed to occur for 2 seconds after which the contact is broken and the cumulative rate for the first 2 seconds is calculated. Apparatus Conditioned Room—Temperature is controlled from 73° F.±2° F. (23° C.±1° C.). Relative Humidity is controlled from 50%±2%

Sample Preparation—Product samples are cut using hydraulic/pneumatic precision cutter into 3.375 inch diameter circles.

Capacity Rate Tester (CRT)—The CRT is an absorbency tester capable of measuring capacity and rate. The CRT consists of a balance (0.001 g), on which rests on a woven grid (using nylon monofilament line having a 0.014" diameter) placed over a small reservoir with a delivery tube in the center. This reservoir is filled by the action of solenoid valves, which help to connect the sample supply reservoir to an intermediate reservoir, the water level of which is monitored by an optical sensor. The CRT is run with a −2 mm water column, controlled by adjusting the height of water in the supply reservoir.

Software—LabView based custom software specific to CRT Version 4.2 or later.

Water—Distilled water with conductivity <10 μS/cm (target <5 μS/cm) @ 25° C.

For this method, a usable unit is described as one finished product unit regardless of the number of plies. Condition all samples with packaging materials removed for a minimum of 2 hours prior to testing. Discard at least the first ten usable units from the roll. Remove two usable units and cut one 3.375-inch circular sample from the center of each usable unit for a total of 2 replicates for each test result. Do not test samples with defects such as wrinkles, tears, holes, etc. Replace with another usable unit which is free of such defects Pre-Test Set-Up
1. The water height in the reservoir tank is set −2.0 mm below the top of the support rack (where the sample will be placed).
2. The supply tube (8 mm I.D.) is centered with respect to the support net.
3. Test samples are cut into circles of 3⅜" diameter and equilibrated at 73° F.±2° F. (23° C.±1° C.). Relative Humidity is controlled from 50%±2% for at least 2 hours.

Test Description
1. After pressing the start button on the software application, the supply tube moves to 0.33 mm below the water height in the reserve tank. This creates a small meniscus of water above the supply tube to ensure test initiation. A valve between the tank and the supply tube closes, and the scale is zeroed.
2. The software prompts you to "load a sample". A sample is placed on the support net, centering it over the supply tube, and with the side facing the outside of the roll placed downward.
3. Close the balance windows, and press the "OK" button—the software records the dry weight of the circle.
4. The software prompts you to "place cover on sample". The plastic cover is placed on top of the sample, on top of the support net. The plastic cover has a center pin (which is flush with the outside rim) to ensure that the sample is in the proper position to establish hydraulic connection. Four other pins, 1 mm shorter in depth, are positioned 1.25-1.5 inches radially away from the center pin to ensure the sample is flat during the test. The sample cover rim should not contact the sheet. Close the top balance window and click "OK".
5. The software re-zeroes the scale and then moves the supply tube towards the sample. When the supply tube reaches its destination, which is 0.33 mm below the support net, the valve opens (i.e., the valve between the reserve tank and the supply tube), and hydraulic connection is established between the supply tube and the sample. Data acquisition occurs at a rate of 5 Hz, and is started about 0.4 seconds before water contacts the sample.
6. The test runs for 2 seconds. After this, the supply tube pulls away from the sample to break the hydraulic connection.
7. The wet sample is removed from the support net. Residual water on the support net and cover are dried with a paper towel.
8. Repeat until all samples are tested.
9. After each test is run, a *.txt file is created (typically stored in the CRT/data/rate directory) with a file name as typed at the start of the test. The file contains all the test set-up parameters, dry sample weight, and cumulative water absorbed (g) vs. time (sec) data collected from the test.
10. Report the average cumulative 0-2 seconds rate to the nearest 0.001 g/second as the CRT Rate.
11. The difference between a Control Sample and a Test Sample can be calculated from their respective CRT Rates from Step 10 and then the percentage change can be determined and reported as CRT Rate Change.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent fibrous structure comprising a polymeric fluid comprising a polymer soil adsorbing agent comprising two or more different monomeric units, wherein the polymer soil adsorbing agent exhibits a weight average molecular weight of from about 50,000 g/mol to about 6,000,000 g/mol as measured according to the Molecular Weight Test Method and a charge density of greater than 0 meq/g as measured according to the Charge Density Test Method.

2. The absorbent fibrous structure according to claim 1 wherein the absorbent fibrous structure exhibits an average Soil Adsorption Value of about 90 mg soil/g absorbent fibrous structure or greater as measured according to the Soil Adsorption Test Method.

3. The absorbent fibrous structure according to claim 1 wherein the absorbent fibrous structure comprises a plurality of pulp fibers.

4. The absorbent fibrous structure according to claim 3 wherein the absorbent fibrous structure comprises a sanitary tissue product.

5. The absorbent fibrous structure according to claim 4 wherein the sanitary tissue product comprises a paper towel.

6. The absorbent fibrous structure according to claim 1 wherein the absorbent fibrous structure comprises a cleaning pad.

7. The absorbent fibrous structure according to claim 1 wherein the absorbent fibrous structure exhibits a moisture level of less than 30% as measured according to the Moisture Content Test Method.

8. The absorbent fibrous structure according to claim 1 wherein the absorbent fibrous structure exhibits an average Mirror Cleaning Densitometer Value of −0.5 or greater as measured according to the Mirror Cleaning Test Method.

9. The absorbent fibrous structure according to claim 1 wherein at least one of the monomeric units is derived from an acrylamide compound.

10. The absorbent fibrous structure according to claim 9 wherein at least one of the monomeric units is derived from a methylene bis acrylamide compound.

11. The absorbent fibrous structure according to claim 10 wherein the polymer soil adsorbing agent comprises less than 200 ppm of the monomeric unit derived from the methylene bis acrylamide compound.

12. The absorbent fibrous structure according to claim 1 wherein the polymer soil adsorbing agent comprises a monomeric unit derived from an acrylamide compound and a monomeric unit derived from a hydroxyalkylacrylate compound.

13. The absorbent fibrous structure according to claim 12 wherein the hydroxyalkylacrylate compound is hydroxypropylacrylate.

14. The absorbent fibrous structure according to claim 12 wherein the polymer soil adsorbing agent comprises less than 50% of the monomeric unit derived from the hydroxyalkylacrylate compound.

15. The absorbent fibrous structure according to claim 1 wherein the polymer soil adsorbing agent is present in the absorbent fibrous structure at a level of from about 0.005% to about 5% by weight of the absorbent fibrous structure.

16. The absorbent fibrous structure according to claim 1 wherein the polymer soil adsorbing agent is present on the fibrous structure in a pattern.

17. The absorbent fibrous structure according to claim 1 wherein the polymeric fluid is in the form of an aqueous solution.

18. The absorbent fibrous structure according to claim 1 wherein the polymeric fluid is in the form of a dispersion or emulsion.

19. The absorbent fibrous structure according to claim 1 wherein the polymeric fluid is in the form of a powder.

20. A method for making an absorbent fibrous structure according to claim 1 wherein the method comprises the step of contacting an absorbent fibrous structure with a polymeric fluid comprising a polymer soil adsorbing agent comprising two or more different monomeric units, wherein the polymer soil adsorbing agent exhibits a weight average molecular weight of from about 50,000 g/mol to about 6,000,000 g/mol as measured according to the Molecular Weight Test Method and a charge density of greater than 0 meq/g as measured according to the Charge Density Test Method.

* * * * *